United States Patent

Beswick et al.

(10) Patent No.: US 7,446,117 B2
(45) Date of Patent: Nov. 4, 2008

(54) COX-2 INHIBITING PYRIDINE DERIVATIVES

(75) Inventors: Paul Beswick, Stevenage (GB); Neil Pegg, Stevenage (GB); Martin Swarbrick, Stevenage (GB); John Skidmore, Stevenage (GB); Sandeep Modi, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 10/527,799

(22) PCT Filed: Sep. 12, 2003

(86) PCT No.: PCT/EP03/11065

§ 371 (c)(1),
(2), (4) Date: Aug. 17, 2005

(87) PCT Pub. No.: WO2004/024691

PCT Pub. Date: Mar. 25, 2004

(65) Prior Publication Data

US 2006/0040988 A1    Feb. 23, 2006

(30) Foreign Application Priority Data

Sep. 16, 2002   (EP) ..................... 0221443

(51) Int. Cl.
A61K 31/4418   (2006.01)
C07D 213/73    (2006.01)
C07D 213/64    (2006.01)

(52) U.S. Cl. ............ 514/352; 514/344; 514/345; 514/348; 514/349; 514/350; 514/351; 546/288; 546/289; 546/290; 546/296; 546/297; 546/300; 546/301; 546/302; 546/303; 546/304; 546/309; 546/310; 546/311; 546/312

(58) Field of Classification Search ......... 514/344, 514/345, 348, 349, 350, 351, 352; 546/288; 546/289, 290, 296, 297, 300, 301, 302, 303, 546/304, 309, 310, 311, 312
See application file for complete search history.

(56) References Cited

U.S. PATENT DOCUMENTS

| | | | |
|---|---|---|---|
| 3,149,109 A | 9/1964 | Ncustaedter et al. |
| 3,592,895 A | 7/1971 | Hepworth et al. |
| 5,474,995 A | 12/1995 | Ducharme et al. |
| 5,760,068 A | 6/1998 | Talley et al. |
| 5,849,758 A | 12/1998 | Kleemann et al. |
| 5,972,842 A | 10/1999 | Maier et al. |
| 5,972,986 A | 10/1999 | Seibert et al. |
| 5,985,886 A | 11/1999 | Elliott et al. |
| 6,020,343 A | 2/2000 | Belley et al. |
| 6,121,202 A | 9/2000 | Karp et al. |
| 6,153,619 A | 11/2000 | Wood et al. |
| 6,248,892 B1 | 6/2001 | Noerenberg et al. |
| 6,306,866 B1 | 10/2001 | Wood et al. |
| 6,313,072 B1 | 11/2001 | Scheiblich et al. |
| 6,355,799 B1 | 3/2002 | Gupta et al. |
| 6,451,794 B1 | 9/2002 | Beswick et al. |
| 6,498,166 B1 | 12/2002 | Campbell et al. |
| 6,756,498 B2 | 6/2004 | Fitzgerald et al. |
| 6,759,413 B2 | 7/2004 | Mangel et al. |
| 6,780,869 B1 | 8/2004 | Green et al. |
| 6,780,870 B2 | 8/2004 | Carter et al. |
| 6,803,463 B2 | 10/2004 | Mathews et al. |
| 6,831,097 B2 | 12/2004 | Beswick et al. |
| 6,861,249 B1 | 3/2005 | Kent |
| 2003/0013717 A1 | 1/2003 | Mangel et al. |
| 2003/0018023 A1 | 1/2003 | Pinto et al. |

FOREIGN PATENT DOCUMENTS

| | | |
|---|---|---|
| CA | 2169231 | 8/1996 |
| DE | 19651099 | 6/1998 |
| DE | 19708928 | 9/1998 |
| DE | 19909541 | 3/1999 |
| DE | 19831246 | 1/2000 |
| EP | 0723960 | 7/1996 |
| EP | 0820996 | 1/1998 |
| GB | 1269484 | 4/1972 |
| JP | 09241161 | 9/1997 |
| JP | 2001252044 | 11/1999 |
| JP | 2000026421 | 1/2000 |
| JP | 2001081074 | 3/2001 |
| WO | WO 94/24110 | 10/1994 |
| WO | WO 96/07641 | 3/1996 |

(Continued)

OTHER PUBLICATIONS

Casanova, B., et al. "A Critical Review of the Current Pathogenesis of Multiple Sclerosis and Possible Future Trends." PubMed Abstract (Rev. Neurol. 28(9):909-915, May 1989.

(Continued)

Primary Examiner—Patricia L Morris
(74) Attorney, Agent, or Firm—J. Scott Young

(57) ABSTRACT

Compounds of formula (I)

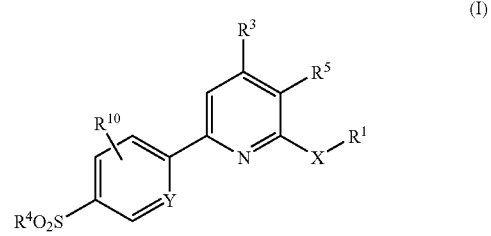

or pharmaceutically acceptable salts thereof are potent and selective inhibitors of COX-2 and are of use in the treatment of the pain, fever and inflammation of a variety of conditions and diseases.

10 Claims, No Drawings

FOREIGN PATENT DOCUMENTS

| | | |
|---|---|---|
| WO | WO 96/24584 | 8/1996 |
| WO | WO 96/24585 | 8/1996 |
| WO | WO 96/41625 | 12/1996 |
| WO | WO 96/41645 | 12/1996 |
| WO | WO 97/37989 | 10/1997 |
| WO | WO 97/38996 | 10/1997 |
| WO | WO 98/03484 | 1/1998 |
| WO | WO 98/16227 | 4/1998 |
| WO | WO 98/24782 | 6/1998 |
| WO | WO 99/01439 | 1/1999 |
| WO | WO 99/12930 | 3/1999 |
| WO | WO 99/55668 | 4/1999 |
| WO | WO 99/21837 | 5/1999 |
| WO | WO 99/42455 | 8/1999 |
| WO | WO 99/55675 | 11/1999 |
| WO | WO 99/64412 | 12/1999 |
| WO | WO 02/26216 | 5/2000 |
| WO | WO 00/47553 A2 | 8/2000 |
| WO | WO 00/52008 | 9/2000 |
| WO | WO 01/38295 | 5/2001 |
| WO | WO 01/38311 | 5/2001 |
| WO | WO 01/41760 | 6/2001 |
| WO | WO 01/45703 | 6/2001 |
| WO | WO 01/46194 | 6/2001 |
| WO | WO 01/56573 | 8/2001 |
| WO | WO 01/58881 | 8/2001 |
| WO | WO 01/62233 | 8/2001 |
| WO | WO 01/83479 | 11/2001 |
| WO | WO 02/00647 | 1/2002 |
| WO | WO 02/00655 | 1/2002 |
| WO | WO 02/07721 | 1/2002 |
| WO | WO 02/18374 | 3/2002 |
| WO | WO 02/44137 | 6/2002 |
| WO | WO 02/055484 | 7/2002 |
| WO | WO 02/059122 | 8/2002 |
| WO | WO 02/096427 | 12/2002 |
| WO | WO 02/096885 | 12/2002 |
| WO | WO 02/096886 | 12/2002 |
| WO | WO 02/100838 | 12/2002 |
| WO | WO 03/004472 | 1/2003 |
| WO | WO 03/14091 | 2/2003 |
| WO | WO 03/014092 | 2/2003 |
| WO | WO 03/022219 | 3/2003 |
| WO | WO 2004/018452 | 3/2003 |
| WO | WO 03/77920 | 9/2003 |
| WO | WO 2004/024691 | 3/2004 |
| WO | WO 2004/048344 | 6/2004 |
| WO | WO 2005/016924 | 2/2005 |

OTHER PUBLICATIONS

Damasio, A.R., et al. Alzheimer's Disease and Related Dementias, Cecil Textbook of Medicine, vol. 2, pp. 1992-1996, 1996.

Douglas, R.G., Jr. Introduction to Viral Diseases: Cecil Textbook of Medicine, 20th Edition, vol. 2, pp. 1739-1747, 1996.

Freston, J.W., et al. Rationalizing Cyclooxygenase (COX) Inhibition for Maximal Efficacy and Minimal Adverse Events + Abstract, Am. J. Med. 107(6A):78S-88S: Discussion 89S), Dec. 1999.

Layzer, R.B., et al. Degenerative Diseases of the Nervous System, Cecil Textbook of Medicine, 20th Edition, vol. 2, pp. 2050-2057, 1996.

Naesdal, J. et al. "Gastro-Duodenal Protection in an Era of Cyclo-Oxygenase-2-Selective Nonsteroidal Anti-inflammatory Drugs." PubMed Abstract, Eur J Gastroenterol Hepatol, 13(12):1401-1406. Dec. 2001.

Simone, JV., Oncology: Introduction, Cecil Textbook of Medicine, 20th Edition, vol. 1, pp. 1004-1010, 1996

Stanghellini, V., et al. "Risk Indicators of Delayed Gastric Emptying of Solids in Patients With Functional Dyspepsia." Gastroenterology, 110, 1996, pp. 1036-1042.

GlaxoSmithKline Internal Report, PAMS Sumary Report for [*54] in HTB In Vivo Screening (1st PAMS) (redacted), May 15, 2005.

GlaxoSmithKline Internal Report, The Cox-2 Inhibitor [*54*] is Effective in Rat Models of Inflammatory Pain (redacted), Jul. 15, 2005.

COX-2 INHIBITING PYRIDINE DERIVATIVES

CROSS REFERENCES TO RELATED APPLICATIONS

This application is a 371 Application of PCT/EP2003/011065, filed 12 Sep. 2003, which claims priority to GB Application Ser. No. 0221443.5 filed 16 Sep. 2002.

This invention relates to pyridine derivatives, to processes for their preparation, to pharmaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is largely responsible for the important physiological functions such as maintenance of gastrointestinal integrity and renal blood flow. In contrast the inducible form, COX-2, is believed to be largely responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1. We have now found a novel group of compounds which are both potent and selective inhibitors of COX-2.

The invention thus provides a compound of formula (I)

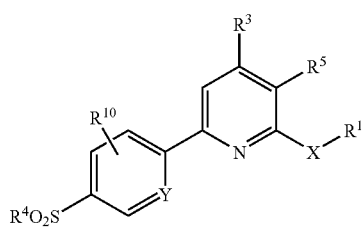

(I)

or a pharmaceutically acceptable salt thereof in which:

X is selected from the group consisting of oxygen or $NR^2$;
Y is selected from the group consisting of CH or nitrogen;
$R^1$ is selected from the group consisting of H, $C_{1-6}$alkyl, $C_{1-2}$alkyl substituted by one to five fluorine atoms, $C_{1-3}$alkyl$OC_{1-3}$alkyl, $C_{3-6}$alkenyl, $C_{3-6}$alkynyl, $C_{3-10}$cycloalkyl$C_{0-6}$alkyl, $C_{4-7}$cycloalkyl substituted by $C_{1-3}$alkyl or $C_{1-3}$alkoxy, $C_{4-12}$bridged cycloalkyl, $A(CR^6R^7)_n$ and $B(CR^6R^7)_n$;
$R^2$ is selected from the group consisting of H and $C_{1-6}$alkyl; or
$R^1$ and $R^2$, together with the nitrogen atom to which they are attached form a 4-8 membered saturated heterocyclic ring such as a pyrrolidine, morpholine or piperidine ring, or a 5-membered heteroaryl ring which is unsubstituted or substituted by one $R^8$;
$R^3$ is selected from the group consisting of $C_{1-5}$alkyl and $C_{1-2}$alkyl substituted by one to five fluorine atoms;
$R^4$ is selected from the group consisting of $C_{1-6}$alkyl, $NH_2$ and $R^9$CONH;
$R^5$ is selected from the group consisting of hydrogen, $C_{1-3}$alkyl, $C_{1-2}$alkyl substituted by one to five fluorine atoms, $C_{1-3}$alkylO$_2$C, halogen, cyano, $(C_{1-3}$alkyl$)_2$NCO, $C_{1-3}$alkylS and $C_{1-3}$alkylO$_2$S;
$R^6$ and $R^7$ are independently selected from H or $C_{1-6}$alkyl;
A is an unsubstituted 5- or 6-membered heteroaryl or an unsubstituted 6-membered aryl, or a 5- or 6-membered heteroaryl or a 6-membered aryl substituted by one or more $R^8$;
$R^8$ is selected from the group consisting of halogen, $C_{1-6}$alkyl, $C_{1-6}$alkyl substituted by one more fluorine atoms, $C_{1-6}$alkoxy, $C_{1-6}$alkoxy substituted by one or more F, $NH_2SO_2$ and $C_{1-6}$alkylSO$_2$;
B is selected from the group consisting of

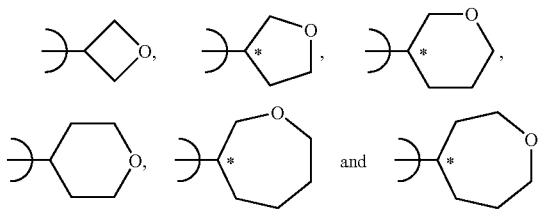

where ) defines the point of attachment of the ring;
$R^9$ is selected from the group consisting of H, $C_{1-6}$alkyl, $C_{1-6}$alkoxy, $C_{1-6}$alkylOC$_{1-6}$alkyl, phenyl, HO$_2$CC$_{1-6}$alkyl, $C_{1-6}$alkylOCOC$_{1-6}$alkyl, $C_{1-6}$alkylOCO, H$_2$NC$_{1-6}$alkyl, $C_{1-6}$alkylOCONHC$_{1-6}$alkyl and $C_{1-6}$alkylCONHC$_{1-6}$alkyl;
$R^{10}$ is selected from the group consisting of H and halogen; and
n is 0 to 4.

The term 'halogen' is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

The term 'saturated heterocyclic' means a saturated ring containing at least one atom other than carbon.

The term '5-membered heteroaryl' means a heteroaryl selected from the following:

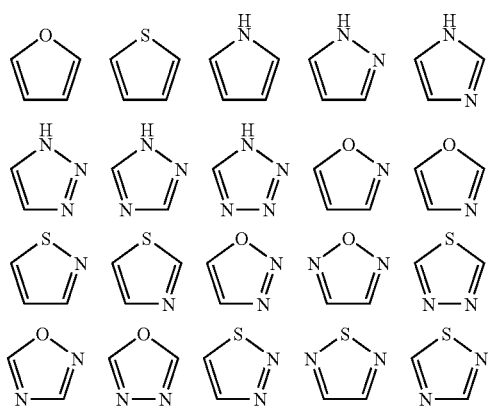

The term '6-membered heteroaryl' means a heteroaryl selected from the following:

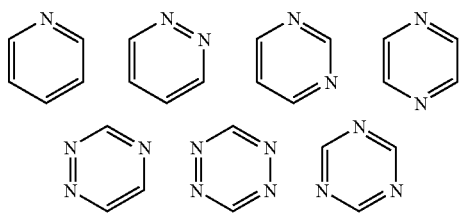

The term '6-membered aryl' means:

It is to be understood that the present invention encompasses all isomers of the compounds of formula (I) and their pharmaceutically acceptable derivatives, including all geometric, tautomeric and optical forms, and mixtures thereof (e.g. racemic mixtures). In particular when the ring B lacks a plane of symmetry the compounds of formula (I) contain a chiral centre as indicated therein by the asterisk *. Furthermore, it will be appreciated by those skilled in the art that when $R^6$ and $R^7$ in formula (I) are different the corresponding compounds contain at least one chiral centre, by virtue of the asymmetric carbon atom defined thereby, and that such compounds exist in the form of a pair of optical isomers (i.e. enantiomers).

It will be appreciated that in some instances, compounds of the present invention may include a basic function such as an amino group as a substituent. Such basic functions may be used to form acid addition salts, in particular pharmaceutically acceptable salts. Pharmaceutically acceptable salts include those described by Berge, Bighley, and Monkhouse, *J. Pharm. Sci.*, 1977, 66, 1-19. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, taurocholic acid, benzenesulfonic, p-toluenesulfonic, hydrochloric, hydrobromic, sulfuric, cyclohexylsulfamic, phosphoric and nitric acids.

It will be appreciated that in some instances, compounds of the present invention may include a carboxy group as a substituent. Such carboxy groups may be used to form salts, in particular pharmaceutically acceptable salts. Pharmaceutically acceptable salts include those described by Berge, Bighley, and Monkhouse, *J. Pharm. Sci.*, 1977, 66, 1-19. Preferred salts include alkali metal salts such as the sodium and potassium salts.

In one aspect the invention provides a compound of formula (IA)

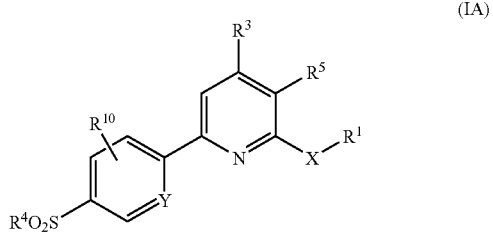

(IA)

or a pharmaceutically acceptable salt thereof in which:

X is selected from the group consisting of oxygen or $NR^2$;
Y is selected from the group consisting of CH or nitrogen;
$R^1$ is selected from the group consisting of H, $C_{1-6}$alkyl, $C_{1-2}$alkyl substituted by one to five fluorine atoms, $C_{1-3}$alkylOC$_{1-3}$alkyl, $C_{3-6}$alkenyl, $C_{3-6}$alkynyl, $C_{3-10}$cycloalkylC$_{0-6}$alkyl, $C_{4-12}$bridged cycloalkyl, $A(CR^6R^7)_n$, and $B(CR^6R^7)_n$;
$R^2$ is selected from the group consisting of H and $C_{1-6}$alkyl; or
$R^1$ and $R^2$, together with the nitrogen atom to which they are attached form a 4-8 membered saturated heterocyclic ring such as a pyrrolidine, morpholine or piperidine ring;
$R^3$ is selected from the group consisting of $C_{1-5}$alkyl and $C_{1-2}$alkyl substituted by one to five fluorine atoms;
$R^4$ is selected from the group consisting of $C_{1-6}$alkyl, $NH_2$ and $R^9CONH$;
$R^5$ is selected from the group consisting of hydrogen, $C_{1-3}$alkyl, $C_{1-2}$alkyl substituted by one to five fluorine atoms, halogen, cyano, $(C_{1-3}alkyl)_2NCO$, $C_{1-3}$alkylS and $C_{1-3}$alkylO$_2$S;
$R^6$ and $R^7$ are independently selected from H or $C_{1-6}$alkyl;
A is an unsubstituted 5- or 6-membered heteroaryl or an unsubstituted 6-membered aryl, or a 5- or 6-membered heteroaryl or a 6-membered aryl substituted by one or more $R^8$;
$R^8$ is selected from the group consisting of halogen, $C_{1-6}$alkyl, $C_{1-6}$alkyl substituted by one more fluorine atoms, $C_{1-6}$alkoxy, $C_{1-6}$alkoxy substituted by one or more F, $NH_2SO_2$ and $C_{1-6}$alkylSO$_2$;
B is selected from the group consisting of

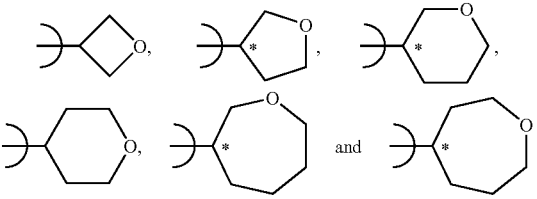

where $\supset$ defines the point of attachment of the ring;
$R^9$ is selected from the group consisting of H, $C_{1-6}$alkyl, $C_{1-6}$alkoxy, $C_{1-6}$alkylOC$_{1-6}$alkyl, phenyl, HO$_2$CC$_{1-6}$alkyl, $C_{1-6}$alkylOCOC$_{1-6}$alkyl, $C_{1-6}$alkylOCO, $H_2NC_{1-6}$alkyl, $C_{1-6}$alkylOCONHC$_{1-6}$alkyl and $C_{1-6}$alkylCONHC$_{1-6}$alkyl;
$R^{10}$ is selected from the group consisting of H and halogen; and
n is 0 to 4.

In another aspect the invention provides a compound of formula (IB)

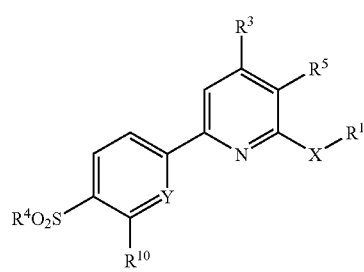

(IB)

or a pharmaceutically acceptable salt thereof, in which all substituents are as for a compound of formula (I) defined hereinabove.

In another aspect the invention provides a compound of formula (IC)

(IC)

or a pharmaceutically acceptable salt thereof in which:

X is selected from the group consisting of oxygen or $NR^2$;

Y is selected from the group consisting of CH or nitrogen;

$R^1$ is selected from the group consisting of H, $C_{1-6}$alkyl, $C_{1-2}$alkyl substituted by one to five fluorine atoms, $C_{1-3}$alkylO$C_{1-3}$alkyl, $C_{3-6}$alkenyl, $C_{3-6}$alkynyl, $C_{3-10}$cycloalkyl$C_{0-6}$alkyl, $C_{4-7}$cycloalkyl substituted by $C_{1-3}$alkyl or $C_{1-3}$alkoxy, $C_{4-12}$bridged cycloalkyl, $A(CR^6R^7)_n$ and $B(CR^6R^7)_n$;

$R^2$ is selected from the group consisting of H and $C_{1-6}$alkyl; or $R^1$ and $R^2$, together with the nitrogen atom to which they are attached form a 4-8 membered saturated heterocyclic ring such as a pyrrolidine, morpholine or piperidine ring, or a 5-membered heteroaryl ring which is unsubstituted or substituted by one $R^8$;

$R^3$ is selected from the group consisting of $C_{1-5}$alkyl and $C_{1-2}$alkyl substituted by one to five fluorine atoms;

$R^4$ is selected from the group consisting of $C_{1-6}$alkyl, $NH_2$ and $R^9$CONH;

$R^5$ is selected from the group consisting of hydrogen, $C_{1-3}$alkyl, $C_{1-2}$alkyl substituted by one to five fluorine atoms, $C_{1-3}$alkylO$_2$C, halogen, cyano, $(C_{1-3}$alkyl$)_2$NCO, $C_{1-3}$alkylS and $C_{1-3}$alkylO$_2$S;

$R^6$ and $R^7$ are independently selected from H or $C_{1-6}$alkyl;

A is an unsubstituted 5- or 6-membered heteroaryl or an unsubstituted 6-membered aryl, or a 5- or 6-membered heteroaryl or a 6-membered aryl substituted by one or more $R^8$;

$R^8$ is selected from the group consisting of halogen, $C_{1-6}$alkyl, $C_{1-6}$alkyl substituted by one more fluorine atoms, $C_{1-6}$alkoxy, $C_{1-6}$alkoxy substituted by one or more F, $NH_2SO_2$ and $C_{1-6}$alkylSO$_2$;

B is selected from the group consisting of where ⊃ defines the point of attachment of the ring;

$R^9$ is selected from the group consisting of H, $C_{1-6}$alkyl, $C_{1-6}$alkoxy, $C_{1-6}$alkylO$C_{1-6}$alkyl, phenyl, HO$_2$C$C_{1-6}$alkyl, $C_{1-6}$alkylOCO$C_{1-6}$alkyl, $C_{1-6}$alkylOCO, $H_2$N$C_{1-6}$alkyl, $C_{1-6}$alkylOCONH$C_{1-6}$alkyl and $C_{1-6}$alkylCONH$C_{1-6}$alkyl;

$R^{10}$ is selected from the group consisting of H and halogen; and n is 1 to 4.

In another aspect of the invention Y is carbon.

In another aspect of the invention $R^1$ is selected from the group consisting of, $C_{1-6}$alkyl, $C_{3-10}$cycloalkyl$C_{0-6}$alkyl, $C_{5-6}$cycloalkyl substituted by $C_{1-2}$alkyl or $C_{1-2}$alkoxy, $C_{1-3}$alkylO$C_{1-3}$alkyl and $C_{1-2}$alkyl substituted by one to five fluorine atoms.

Representative examples of $R^1$ include cyclohexylmethyl, cyclohexyl, n-butyl, n-pentyl, cyclopentyl, 2-methylpropyl, 2,2-dimethylpropyl, 2,2,2-trifluoroethyl, 2-methoxyethyl and ethyl.

Further representative examples of $R^1$ include 1-methylethyl, 1-ethylpropyl, cycloheptyl, cis-4-methylcyclohexyl, trans-4-methylcyclohexyl, cyclobutyl, cyclopentanemethyl, and trans-4-(ethoxy)cyclohexyl.

In another aspect of the invention $R^1$ is selected from the group consisting of $A(CR^6R^7)_n$ and $B(CR^6R^7)_n$.

Further representative examples of $R^1$ include benzyl, 4-chlorobenzyl, 2-furylmethyl, 4-methylphenyl, 4-fluorophenyl, 4-methoxyphenyl, 3-pyridyl, 2-chlorophenyl, 3,5-difluorobenzyl, 3-pyridylmethyl, 2-methylbenzyl, 2-chlorobenzyl, (S)-α-methylbenzyl, (R)-α-methylbenzyl, 6-methylpyridin-3-yl, 4-methoxybenzyl, 4-fluorobenzyl, 2-(5-methylfuryl)methyl, 4-methylbenzyl, 4-pyridylmethyl, 2-pyridylmethyl, 2-(6-methylpyridine)methyl, 2-thiophenylmethyl, 4-pyranylmethyl, 2-tetrahydrofurylmethyl, 2-(5-methylpyrazine)methyl and 4-ethoxybenzyl.

Further representative examples of $R^1$ include 1H-imidazol-2-ylmethyl, 1H-pyrazol-4-ylmethyl, (1-methyl-1H-imidazol-2-yl)methyl, (3-methyl-1H-pyrazol-4-yl)methyl, (1-methyl-1H-pyrazol-3-yl)methyl, (1-methyl-1H-pyrazol-4-yl)methyl, (3-methyl-1H-pyrazol-5-yl)methyl, (1-methyl-1H-pyrazol-5-yl)methyl, (1-methyl-1H-1,2,4-triazol-5-yl)methyl, (5-methyl-3-isoxazolyl)methyl, tetrahydro-2H-pyran-4-yl, tetrahydro-2H-pyran-4-ylmethyl, (6-methyl-3-pyridyl)methyl, 2-pyrazinylmethyl, (2-methyl-1H-imidazol-4-yl)methyl, (4-methyl-1H-imidazol-5-yl)methyl, (4-methyl-1H-imidazol-2-yl)methyl, (1-ethyl-1H-imidazol-2-yl)methyl, (1,3-dimethyl-1H-pyrazol-4-yl)methyl, (1,5-dimethyl-1H-pyrazol-4-yl)methyl, (3-methyl-5-isothiazolyl)methyl, (4-methyl-1,3-thiazol-2-yl)methyl, (3-methyl-4-isothiazolyl)methyl, [1-(fluoromethyl)-1H-pyrazol-4-yl]methyl, (2-methyl-3-pyridyl)methyl, (6-methyl-3-pyridyl)methyl, (1-methyl-1H-imidazol-2-yl)methyl, (5-chloro-2-pyridyl)methyl, 1H-imidazol-2-ylmethyl, 4-ethoxyphenyl, 3-chloro-4-methylphenyl, (5-chloro-2-pyridyl)methyl, (6-methyl-3-pyridyl)methyl, 2-methyl-3-pyridyl, 6-methyl-2-pyridyl, 2-pyrazinylmethyl, 2,6-dimethyl-3-pyridyl, 3,4-dichlorobenzyl, 5-chloro-3-pyridyl, 6-chloro-3-pyridazinyl, 3,5-dichlorobenzyl, 2-carboxyphenyl, (5-methyl-2-pyridyl)methyl, 4-chloro-3-(trifluoromethyl)benzyl, (5-bromo-2-pyridyl)methyl, (4-bromo-4-pyridyl)methyl, (3-methyl-4-isoxazolyl)methyl, 5-pyrimidinylmethyl, (3-methyl-1,2,4-oxadiazol-5-yl)methyl, (5-methyl-1,2,4-oxadiazol-3-yl)methyl and (1-ethyl-1H-1,2,4-triazol-5-yl)methyl.

In another aspect of the invention $R^1$ is selected from the group consisting of $C_{3-6}$alkenyl and $C_{3-6}$alkynyl.

Further representative examples of $R^1$ include propargyl and allyl.

In another aspect of the invention $R^2$ is H or $C_{1-2}$alkyl.

Representative examples of $R^2$ include H, methyl and ethyl.

In another aspect of the invention $R^3$ is $CHF_2$, $CH_2F$, $CF_3$ or $C_{1-4}$alkyl.

Representative examples of $R^3$ include $CF_3$, $CH_3$ and ethyl.

Further representative examples of $R^3$ include $CH_2F$.

In another aspect of the invention $R^4$ is $C_{1-6}$alkyl, such as $C_{1-3}$alkyl.

Representative examples of $R^4$ include $CH_3$.

In another aspect of the invention $R^4$ is $NH_2$.

Further representative examples of $R^4$ include $NH_2$.

In another aspect of the invention $R^5$ is hydrogen or $C_{1-3}$alkyl.

Representative examples of $R^5$ include H or $CH_3$.

In another aspect of the invention $R^5$ is CN, halogen or $CO_2Et$.

Further representative examples of $R^5$ include CN, F, Cl, $CO_2Et$.

In another aspect of the invention $R^6$ and $R^7$ are independently selected from H or methyl. In another aspect $R^6$ and $R^7$ are both H.

In another aspect of the invention A is selected from the group consisting of

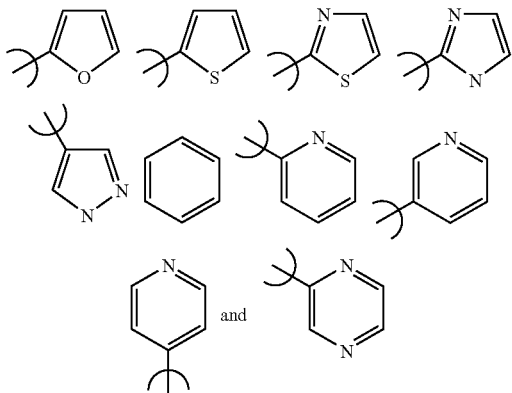

where ⊃ defines the point of attachment of the ring and A is unsubstituted or substituted by one or two $R^8$.

In another aspect of the invention A is selected from the group consisting of

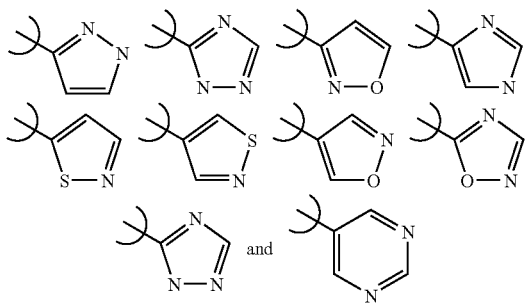

where ⊃ defines the point of attachment of the ring

In another aspect of the invention $R^8$ is selected from the group consisting of halogen, $C_{1-3}$alkyl, $C_{1-3}$alkyl substituted by one to three fluorine atoms (e.g. $CF_3$), and $C_{1-3}$alkoxy.

Representative examples of $R^8$ include F, Cl, $CH_3$, methoxy and ethoxy.

Further representative examples of $R^8$ include ethyl, fluoromethyl, $CF_3$ and Br.

Representative examples of B include

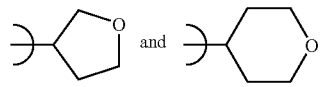

In another aspect of the invention $R^9$ is selected from the group consisting of $C_{1-6}$alkyl (e.g. ethyl), phenyl and aminomethyl.

In another aspect of the invention $R^{10}$ is H.

In another aspect of the invention in compounds of formula (I), (IA) and (IB) n is 0 to 2 (e.g. 1) or in compounds of formula (IC) n is 1 or 2.

In another aspect the invention provides a compound of formula (I) or a pharmaceutically acceptable salt thereof in which:

X is oxygen;
Y is CH;
$R^1$ is $A(CR^6R^7)_n$;
$R^3$ is selected from the group consisting of $C_{1-5}$alkyl and $C_{1-2}$alkyl substituted by one to five fluorine atoms;
$R^4$ is $C_{1-6}$alkyl;
$R^5$ is selected from the group consisting of hydrogen, $C_{1-3}$alkyl, $C_{1-2}$alkyl substituted by one to five fluorine atoms, $C_{1-3}$alkyl$O_2C$, halogen, and $C_{1-3}$alkylS;
A is an unsubstituted 5- or 6-membered heteroaryl or an unsubstituted 6-membered aryl, or a 5- or 6-membered heteroaryl or a 6-membered aryl substituted by one or more $R^8$;
$R^8$ is selected from the group consisting of halogen, $C_{1-6}$alkyl, $C_{1-6}$alkyl substituted by one more fluorine atoms, $C_{1-6}$alkoxy, and $C_{1-6}$alkoxy substituted by one or more F;
$R^{10}$ is selected from the group consisting of H and halogen; and
n is 0.

Preferred compounds of the invention are:
4-ethyl-6-[4-(methylsulfonyl)phenyl]-N-(tetrahydro-2H-pyran-4-ylmethyl)-2-pyridinamine; 4-methyl-N-[(1-methyl-1H-pyrazol-4-yl)methyl]-6-[4-(methylsulfonyl)phenyl]-2-pyridinamine;

N-[(1,5-dimethyl-1H-pyrazol-4-yl)methyl]-4-methyl-6-[4-(methylsulfonyl)phenyl]-2-pyridinamine;

N-[(1,3-dimethyl-1H-pyrazol-4-yl)methyl]-4-methyl-6-[4-(methylsulfonyl)phenyl]-2-pyridinamine;

4-(6-{[(1,3-dimethyl-1H-pyrazol-4-yl)methyl]amino}-4-ethyl-2-pyridinyl)benzenesulfonamide;

N-[(1,3-dimethyl-1H-pyrazol-4-yl)methyl]-6-[4-(methylsulfonyl)phenyl]-4-(trifluoromethyl)-2-pyridinamine;

N-[(1,5-dimethyl-1H-pyrazol-4-yl)methyl]-6-[4-(methylsulfonyl)phenyl]-4-(trifluoromethyl)-2-pyridinamine;

4-{4-methyl-6-[(tetrahydro-2H-pyran-4-ylmethyl)amino]-2-pyridinyl}benzenesulfonamide;

4-methyl-N-[(1-methyl-1H-pyrazol-3-yl)methyl]-6-[4-(methylsulfonyl)phenyl]-2-pyridinamine;

N-(cyclohexylmethyl)-6-[4-(methylsulfonyl)phenyl]-4-(trifluoromethyl)-2-pyridinamine;

N-cyclohexyl-6-[4-(methylsulfonyl)phenyl]-4-(trifluoromethyl)-2-pyridinamine;

2-[4-(methylsulfonyl)phenyl]-6-[(2-pyridinylmethyl)oxy]-4-(trifluoromethyl)pyridine;

4-methyl-N-[(3-methyl-4-isoxazolyl)methyl]-6-[4-(methylsulfonyl)phenyl]-2-pyridinamine;
6-[4-(methylsulfonyl)phenyl]-N-(2-pyridinylmethyl)-4-(trifluoromethyl)-2-pyridinamine;
N-cycloheptyl-6-[4-(methylsulfonyl)phenyl]-4-(trifluoromethyl)-2-pyridinamine;
N-(cis-4-methylcyclohexyl)-6-[4-(methylsulfonyl)phenyl]-4-(trifluoromethyl)-2-pyridinamine;
N-(1-ethylpropyl)-6-[4-(methylsulfonyl)phenyl]-4-(trifluoromethyl)-2-pyridinamine;
N-[(3-methyl-1,2,4-oxadiazol-5-yl)methyl]-6-[4-(methylsulfonyl)phenyl]-4-(trifluoromethyl)-2-pyridinamine;
N-[(5-methyl-1,2,4-oxadiazol-3-yl)methyl]-6-[4-(methylsulfonyl)phenyl]-4-(trifluoromethyl)-2-pyridinamine;
4-methyl-N-[(1-methyl-1H-pyrazol-5-yl)methyl]-6-[4-(methylsulfonyl)phenyl]-2-pyridinamine;
N-(cyclopentylmethyl)-6-[4-(methylsulfonyl)phenyl]-4-(trifluoromethyl)-2-pyridinamine;
N-[(1-ethyl-1H-1,2,4-triazol-5-yl)methyl]-4-methyl-6-[4-(methylsulfonyl)phenyl]-2-pyridinamine;
4-ethyl-6-[4-(methylsulfonyl)phenyl]-2-[(2-pyridinylmethyl)amino]-3-pyridinecarbonitrile;
4-ethyl-2-{[(5-methyl-2-pyridinyl)methyl]amino}-6-[4-(methylsulfonyl)phenyl]-3-pyridinecarbonitrile;
4-ethyl-2-{[(6-methyl-3-pyridinyl)methyl]amino}-6-[4-(methylsulfonyl)phenyl]-3-pyridinecarbonitrile;
4-ethyl-2-{[(1-methyl-1H-pyrazol-4-yl)methyl]amino}-6-[4-(methylsulfonyl)phenyl]-3-pyridinecarbonitrile;
4-ethyl-6-[4-(methylsulfonyl)phenyl]-2-{[(4-methyl-1,3-thiazol-2-yl)methyl]amino}-3-pyridinecarbonitrile;
4-ethyl-6-[4-(methylsulfonyl)phenyl]-2-[(2-pyridinylmethyl)oxy]-3-pyridinecarbonitrile;
4-ethyl-N-[(1-ethyl-1H-1,2,4-triazol-5-yl)methyl]-6-[4-(methylsulfonyl)phenyl]-2-pyridinamine;
4-ethyl-2-{[(6-methyl-3-pyridinyl)methyl]oxy}-6-[4-(methylsulfonyl)phenyl]-3-pyridinecarbonitrile;
6-[4-(methylsulfonyl)phenyl]-N-[(1-methyl-1H-1,2,4-triazol-5-yl)methyl]-4-(trifluoromethyl)-2-pyridinamine.

Particularly preferred compounds of the invention are:
N-cyclohexyl-6-[4-(methylsulfonyl)phenyl]-4-(trifluoromethyl)-2-pyridinamine;
2-[4-(methylsulfonyl)phenyl]-6-[(2-pyridinylmethyl)oxy]-4-(trifluoromethyl)pyridine;
4-methyl-N-[(1-methyl-1H-pyrazol-4-yl)methyl]-6-[4-(methylsulfonyl)phenyl]-2-pyridinamine.

It is to be understood that the invention covers all combinations of particular aspects of the invention as described hereinabove.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compound of formula (I) may be used for preparing the more pure forms used in pharmaceutical compositions. Although the purity of intermediate compounds of the present invention is less critical, it will be readily understood that the substantially pure form is preferred as for the compounds of formula (I). Preferably, whenever possible, the compounds of the present invention are available in crystalline form.

When some of the compounds of this invention are allowed to crystallise or are recrysallised from organic solvents, solvent of recrystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all the polymorphic forms of the compounds of formula (I).

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases mediated by selective inhibition of COX-2. Such conditions and diseases are well known in the art and include rheumatic fever; symptoms associated with influenza or other viral infections, such as the common cold; lower back and neck pain; headache; toothache; sprains and strains; myositis; sympathetically maintained pain; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

The compounds of the invention are also useful for the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of the invention are also useful for the treatment of other conditions mediated by selective inhibition of COX-2.

For example, the compounds of the invention inhibit cellular and neoplastic transformation and metastatic tumour growth and hence are useful in the treatment of certain cancerous diseases, such as colonic cancer and prostate cancer. The compounds of the invention are also useful in reducing the number of adenomatous colorectal polyps and thus reduce the risk of developing colon cancer. The compounds of the invention are also useful in the treatment of cancer associated with overexpression of HER-2/neu, in particular breast cancer.

Compounds of the invention also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures).

Compounds of the invention also inhibit prostanoid-induced smooth muscle contraction and hence are of use in the treatment of dysmenorrhoea and premature labour.

Compounds of the invention are also useful in the treatment of liver disease, such as inflammatory liver disease, for example chronic viral hepatitis B, chronic viral hepatitis C, alcoholic liver injury, primary biliary cirrhosis, autoimmune hepatitis, nonalcoholic steatohepatitis and liver transplant rejection.

Compounds of the invention inhibit inflammatory processes and therefore are of use in the treatment of asthma, allergic rhinitis and respiratory distress syndrome; gastrointestinal conditions such as inflammatory bowel disease, Crohn's disease, gastritis, irritable bowel syndrome and ulcerative colitis; and the inflammation in such diseases as vascular disease, migraine, periarteritis nodosa, thyroiditis, aplastic anaemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention are also useful in the treatment of ophthalmic diseases such as retinitis, retinopathies, uveitis and of acute injury to the eye tissue.

Compounds of the invention are also useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with aging, particularly Age Associated Memory Impairment.

Compounds of the invention are also useful in the treatment of disorders ameliorated by a gastroprokinetic agent. Disorders ameliorated by gastroprokinetic agents include ileus, for example post-operative ileus and ileus during sepsis; gastroesophageal reflux disease (GORD, or its synonym GERD); gastroparesis, such as diabetic gastroparesis; and other functional bowel disorders, such as non-ulcerative dyspepsia (NUD) and non-cardiac chest pain (NCCP).

According to a further aspect of the invention, we provide a compound of formula (I) for use in human or veterinary medicine.

According to a further aspect of the invention, we provide a method of treating a human or animal subject suffering from a condition which is mediated by COX-2 which comprises administering to said subject an effective amount of a compound of formula (I).

According to a further aspect of the invention, we provide a method of treating a human or animal subject suffering from an inflammatory disorder, which method comprises administering to said subject an effective amount of a compound of formula (I).

According to another aspect of the invention, we provide the use of a compound of formula (I) for the manufacture of a therapeutic agent for the treatment of a condition which is mediated by COX-2.

According to another aspect of the invention, we provide the use of a compound of formula (I) for the manufacture of a therapeutic agent for the treatment of an inflammatory disorder.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor α; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine. It is to be understood that the present invention covers the use of a compound of formula (I) in combination with one or more other therapeutic agents.

The compounds of formula (I) are conveniently administered in the form of pharmaceutical compositions. Thus, in another aspect of the invention, we provide a pharmaceutical composition comprising a compound of formula (I) adapted for use in human or veterinary medicine. Such compositions may conveniently be presented for use in conventional manner in admixture with one or more physiologically acceptable carriers or excipients.

As will be appreciated by the person skilled in the art the compounds of the invention may be milled using known milling procedures such as wet milling to obtain a particle size appropriate for tablet formation and for other formulation types. In particular, for those compounds which demonstrate poor bioavailability, finely divided (nanoparticulate) preparations of the compounds of the invention may be prepared by processes known in the art, for example see International Patent Application No. WO 02/00196 (SmithKline Beecham).

The compounds of formula (I) may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I).

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) may be prepared by any method known in the art for the preparation of compounds of analogous structure.

Compounds of formula (I) may be prepared by a process which comprises:

reacting a compound $R^1XH$ of formula (II), or a protected derivative thereof, with a compound of formula (III)

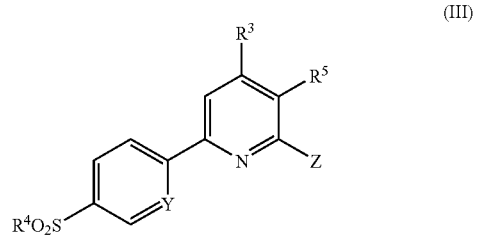

where X is as defined and Z is halogen, such as F, Cl, Br or I, or a sulfonate, such as (4-methyl)benzenesulfonate or trifluoromethanesulfonate and thereafter and if necessary, interconverting a compound of formula (I) into another compound of formula (I); and/or deprotecting a protected derivative of compound of formula (I).

The overall synthesis of a compound of formula (I) is shown in Scheme 1 below in which, $R^1$ to $R^3$, $R^5$, X and Y are as defined in formula (I) unless otherwise stated, $R^4$ is $C_{1-6}$alkyl and Z is a halogen, such as F, Cl, Br or I, or a sulfonate, such as (4-methyl)benzenesulfonate or trifluoromethanesulfonate; LDA is lithium diisopropylamide; THF is tetrahydrofuran.

Referring to Scheme 1, pyridines of formula (I) where $R^5$=Cl can be obtained by treatment of pyridines of formula (I) where $R^5$=H with a chlorinating agent, such as N-chlorosuccinimide, in a solvent, such as acetic acid and at ambient temperature.

Referring to Scheme 1, when $X=NR^2$, compounds of formula (I) may be prepared via the treatment of compounds of formula (III) with an amine of formula (II). This is conveniently carried out in a solvent, such as a nitrile (e.g. methylnitrile) and at elevated temperature (e.g. from about 50° C. to reflux). An excess of the amine may be used in place of the solvent.

Alternatively, the treatment of compounds of formula (III) with an amine of formula (II) is conveniently carried out in a solvent, such as a tertiary amine (e.g. NMP, N-methylpyrrolidinone) and at elevated temperature (e.g. from 120° C. to 250° C.) and with or without microwave irradiation.

Alternatively, the treatment of compounds of formula (III) with an amine of formula (II) may be carried out in the presence of a catalytic quantity of a palladium salt, such as palladium (II) acetate, a phosphine ligand, such as 2,2'-bis (diphenylphosphino)-1,1'-binaphthyl (BINAP), and a base, such as cesium carbonate or sodium tert-butoxide. The reaction is conveniently carried out in a solvent such as toluene or 1,4-dioxan and at elevated temperature.

Scheme 1

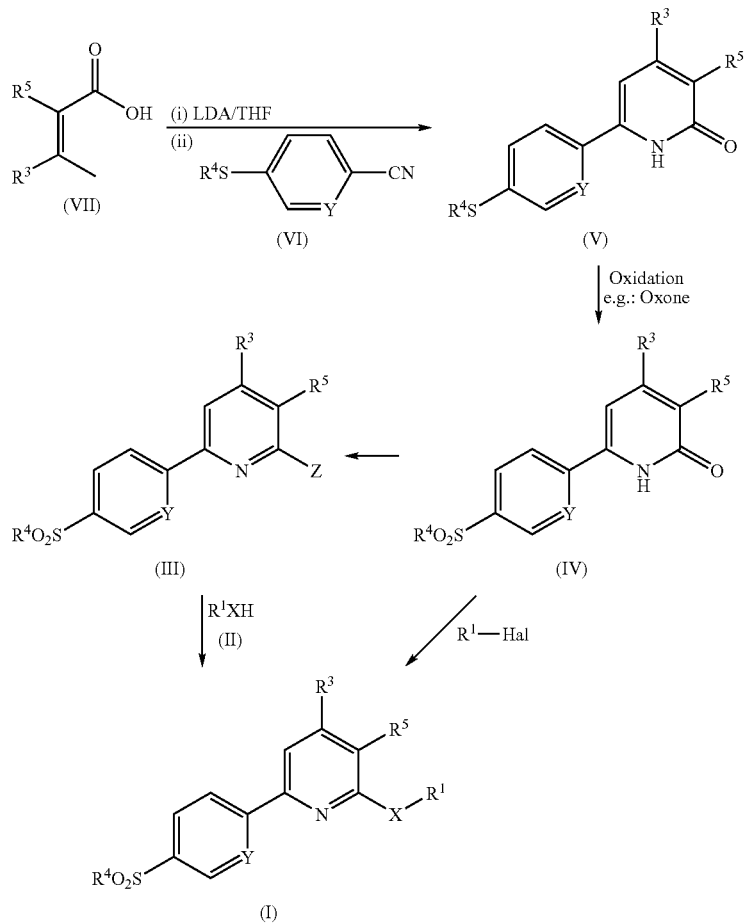

Alternatively, the treatment of compounds of formula (III) with an amine of formula (II) may be carried out in the presence of a base, such as sodium hydride. The reaction is conveniently carried out in a solvent, such as THF, DMF (N,N-dimethylformamide) or NMP (N-methylpyrrolidinone), at between ambient and elevated temperature (e.g. elevated temperature) and with or without microwave irradiation.

Referring to Scheme 1, when X=O, compounds of formula (I) may be prepared by the treatment of compounds of formula (III) with an alcohol of formula (II) in the presence of a base such as sodium hydride. The reaction is conveniently carried out in a solvent such as THF and at between ambient temperature and reflux.

Alternatively, when X=O, compounds of formula (I) may be prepared by treatment of 2-pyridones of formula (IV) with an alkyl halide in the presence of a base, such as silver carbonate, and in a solvent, such as DMF (N,N-dimethylformamide) or n-pentane.

Alternatively, when X=O, 2-pyridones of formula (IV) may be converted to compounds of formula (I) by a Mitsunobu reaction, employing an alcohol of formula (II), a dialkylazodicarboxylate, such as diisopropylazodicarboxylate, a trialkyl- or triarylphosphine, such as tributylphosphine or triphenylphosphine. The reaction is conveniently carried out in a solvent, such as chloroform or THF.

Referring to Scheme 1, 2-pyridones of formula (IV) where $R^5$=H can be converted to 2-pyridones of formula (IV) where $R^5$=F by treatment with a fluorinating agent, such as SELECTFLUOR™ [1-(chloromethyl)-4-fluoro-1,4,-diazoniabicyclo[2.2.2]octane bis-tetrafluoroborate], in a solvent such as acetonitrile, and at between ambient and elevated temperature (eg elevated temperature)

Referring to Scheme 1, 2-pyridones of formula (IV) where $R^5$=H can be converted to 2-pyridones of formula (IV) where $R^5$=Cl or Br by treatment with a halogenating agent, such as N-chlorosuccinimide or N-bromosuccinimide, in a solvent, such as acetic acid and at ambient temperature.

Referring to Scheme 1, the conversion of 2-pyridones of formula (IV) to the corresponding pyridines of formula (III) where Z is chlorine or bromine, is conveniently carried out employing a phosphorous halide species (e.g. phosphorous (V) chloride) in a solvent, such as a phosphorous oxyhalide (e.g. phosphorous oxychloride), and at between ambient and elevated temperature (e.g. elevated temperature). Compounds of formula (III) where Z is chlorine or bromine may be converted to compounds of formula (III) where Z is fluorine or iodine using standard interconversion techniques such as those described in 'Comprehensive Organic Transformations: a guide to functional group preparations' by Richard Larock (VCH, 1989), incorporated herein by reference.

Alternatively, the conversion of 2-pyridones of formula (IV) to the corresponding pyridines of formula (III) where Z is a sulfonate, is conveniently carried out in a solvent, such as a nitrogen-containing solvent (e.g. pyridine) and employing a reagent such as a sulfonyl halide (e.g. (4-methyl)benzenesulfonyl chloride) or a sulfonic anhydride (e.g. trifluoromethanesulfonic anhydride).

Conveniently the oxidation shown in Scheme 1 is carried out using a monopersulfate compound, such as potassium peroxymonopersulfate (known as Oxone™) and the reaction is carried out in a solvent, such as an aqueous alcohol (e.g. aqueous methanol) and at between −78° C. and ambient temperature.

Alternatively, the oxidation shown in Scheme 1 may be effected using hydrogen peroxide in the presence of sodium tungstate dihydrate. The reaction may be carried out in a solvent such as acetic acid and at between ambient temperature and reflux (e.g. 50° C.).

Referring to Scheme 1, pyridones of formula (V) are conveniently prepared by treating α,β-unsaturated acids of formula (VII) with two equivalents of LDA in THF at −78° C., followed by a nitrile of formula (VI), according to the procedure described by E. M. Brown, S. Gil, R. Mestres and M. Pavra in *Synthesis*, 2000, 2, pp 273-280, incorporated herein by reference.

Alternatively, pyridones of formulae (IV) and (V) may be prepared as shown in Scheme 2 below.

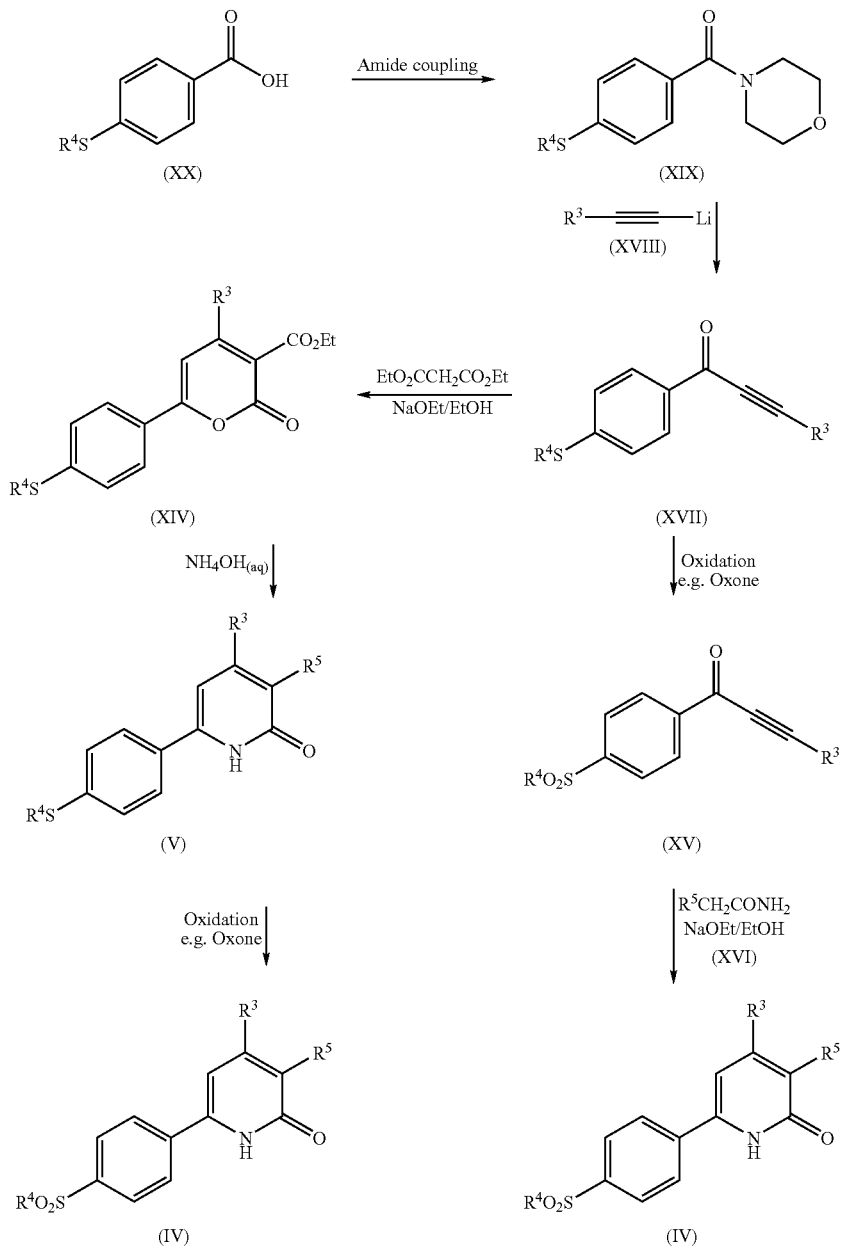

Referring to Scheme 2, compounds of formula (V) (R⁵=H) may be prepared by treatment of compounds of formula (XIV) with ammonia. The reaction is conveniently carried out in a mixture of concentrated aqueous ammonia and dioxane at elevated temperature and in a sealed vessel.

Referring to Scheme 2, compounds of formula (XIV) may be obtained by treatment of compounds of formula (XVII) with a dialkyl malonate (e.g. diethyl malonate) in the presence of a base, such as sodium hydride or a metal alkoxide (e.g. sodium ethoxide). The reaction is conveniently carried out in a solvent, such as THF or an alcohol (e.g. ethanol).

Referring to Scheme 2, compounds of formula (IV) (R⁵≠H) may be prepared by treatment of compounds of formula (XV) with a compound of formula (XVI) in the presence of a base, such as sodium hydride or a metal alkoxide (e.g. sodium ethoxide). The reaction is conveniently carried out in a solvent, such as THF or an alcohol (e.g. ethanol).

Referring to Scheme 2 compounds of formula (XIX) may be converted to compounds of formula (XVII) by treatment with an alkynylmetal species, such as an alkynyllithium species or an alkynyl Grignard reagent. The reaction is conveniently carried out in a solvent, such as THF, and at between −78° C. and ambient temperature.

Referring to Scheme 2, compounds of formula (XIX) may be obtained by treatment of compounds of formula (XX) with morpholine in the presence of an amide coupling reagent, such as dicyclohexylcarbodiimide (DCC) or 1-(3-dimethylaminopropyl)-3-ethylcarbodiimide hydrochloride (EDC) in a solvent such as THF. The reaction may also be carried out in the presence of a base, such as triethylamine or (N,N-diisopropyl)ethylamine.

The synthesis of an intermediate of formula (III) in which R³, R⁵ and Y are as defined for compounds of formula (I), Z is a halogen, such as F, Cl, Br or I, or a sulfonate such as (4-methyl)benzenesulfonate or trifluoromethanesulfonate, and R⁴ is NH₂, is shown in Scheme 3 below. P represents a suitable protecting group.

Referring to Scheme 3, compounds of formula (IX) may be prepared from compounds of formula (VII) in an analogous manner to that described in Scheme 1. Protection of the sulfonamide functionality of the benzonitrile (VIII) may be achieved using a silicon protecting group, such as the 2-(trimethylsilyl)-ethoxymethyl (SEM) group which can be introduced under standard conditions.

Referring to Scheme 3, the conversion of 2-pyridones of formula (IX) to the corresponding pyridines of formula (III) where Z is halogen, is conveniently carried out employing a phosphorous halide species (e.g. phosphorous (V) chloride) in a solvent, such as a phosphorous oxyhalide (e.g. phosphorous oxychloride), and at between ambient and elevated temperature (e.g. elevated temperature).

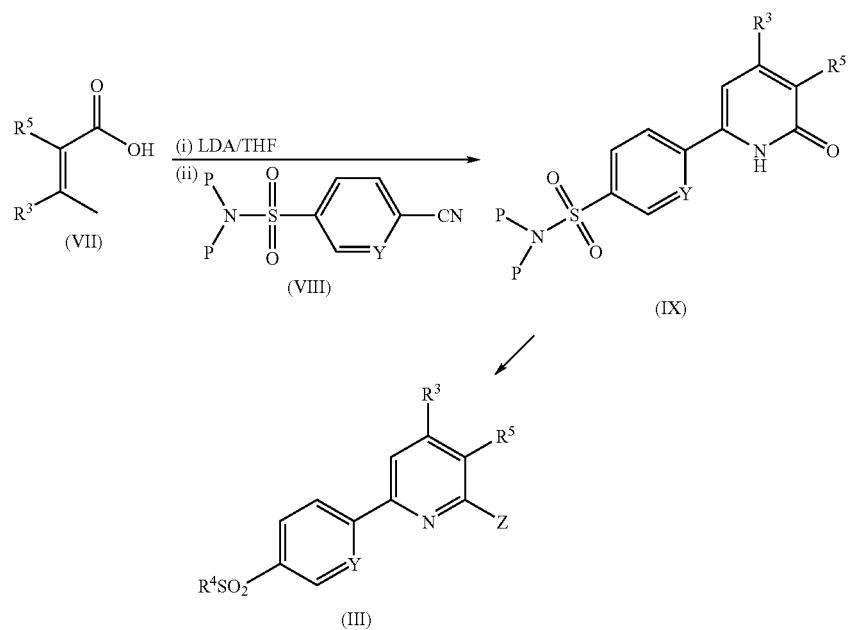

Scheme 3

Alternatively, the conversion of 2-pyridones of formula (IX) to the corresponding pyridines of formula (III) where Z is a sulfonate, is conveniently carried out in a solvent, such as a nitrogen-containing solvent (e.g. pyridine) and employing a reagent such as a sulfonyl halide (e.g. (4-methyl)benzenesulfonyl chloride) or a sulfonic anhydride (e.g. trifluoromethanesulfonic anhydride).

In all alternatives described hereinabove in relation to Scheme 3 for the conversion of (IX) to (III), removal of the protecting groups can be achieved using a source of fluoride, such as tetrabutylammonium fluoride (TBAF), in a suitable organic solvent such as THF, at a temperature between ambient and reflux.

Conversion of the intermediates of formula (III) to compounds of formula (I) can be achieved as described for Scheme 1. In one variation the nitrogen protecting groups on the sulfonamide functionality may be retained during the transformation of intermediates of formula (III) to compounds of formula (I). In some circumstances removal of the protecting groups occurs during the treatment of intermediate (III) with R¹XH (II). Alternatively, the protecting groups may be removed after treatment of (III) with (II) using the standard deprotection conditions described above.

In one variation of Scheme 1, compounds of formula (III) in which Z is halogen, such as F, Cl, Br and I and Y=C, may be synthesised according to Scheme 4 below. $R^1$ to $R^3$, $R^5$ and Y are as defined in formula (I) unless otherwise stated, $R^4$ is $C_{1-6}$alkyl, M represents $B(OH)_2$ or $B(OR)_2$ and m is 0, 1 or 2.

atoms, may be prepared from 2-chloroisonicotinic acid by standard transformations. For example, when $R^3$ is $CH_2F$ or $CHF_2$, this can be conveniently achieved by reduction of 2-chloroisonicotinic acid using borane followed by fluorination of the resulting alcohol using a suitable reagent such as DAST, or oxidation of the alcohol, followed by fluorination of the resulting aldehyde with a suitable reagent such as DAST.

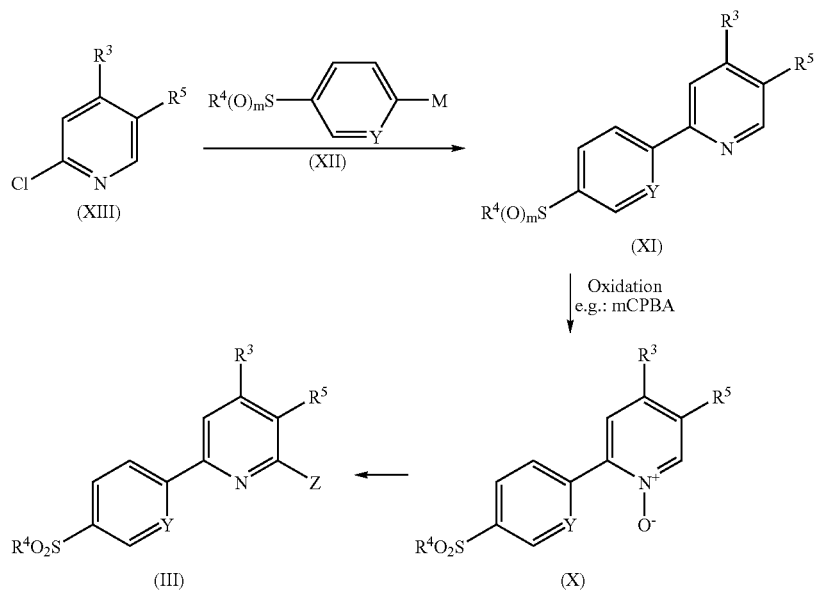

Scheme 4

Referring to Scheme 4, compounds of formula (XIII) may be converted to compounds of formula (XI) via a Suzuki coupling reaction employing a palladium source, such as palladium tetrakistriphenylphosphine $Pd(PPh_3)_4$, or $Pd_2(dba)_3$ and a ligand, such as triphenylphosphine or tri(tertbutyl)phosphine, and a base, such as sodium carbonate, potassium phosphate or potassium fluoride, in a solvent such as a water/toluene mix, a water/dimethoxyethane mix or 1,4-dioxan.

Conveniently, the oxidation shown in Scheme 4 is carried out using 3-chloroperoxybenzoic acid (m-CPBA) in a chlorinated solvent, such as dichloromethane or chloroform, or a mixture of a chlorinated solvent and aqueous sodium bicarbonate ($NaHCO_3$). The oxidation is performed at between 0° C. and ambient temperature.

Alternatively, the oxidation shown in Scheme 4 may be conveniently carried out in a two-step process, treating compounds of formula (XI) (m=0) firstly with oxone, and secondly with mCPBA in a chlorinated solvent, such as dichloromethane or chloroform, or a mixture of a chlorinated solvent and aqueous sodium bicarbonate ($NaHCO_3$). The oxidation is performed at between 0° C. and ambient temperature.

The transformation of (X) to the intermediate (III) may conveniently be achieved via treatment of (X) with a phosphorous halide species (e.g. phosphorous (V) chloride) in a solvent, such as a phosphorous oxyhalide (e.g. phosphorous oxychloride), and at between ambient and elevated temperature (e.g. elevated temperature).

Pyridines of formula (XIII) are either known compounds or, when $R^3$ is $C_{1-2}$alkyl substituted by one to five fluorine It will be appreciated by those skilled in the art that certain of the procedures described in Schemes 1 to 4 for the preparation of compounds of the formula (I) or intermediates thereto may not be applicable to some of the possible substituents.

It will be further appreciated by those skilled in the art that it may be necessary to carry out the transformations described in Schemes 1 to 4 in a different order from that described, or to modify one or more of the transformations, to provide the desired compound of formula (I).

It will be appreciated by those skilled in the art that compounds of formula (I) may be prepared by interconversion, utilising other compounds of formula (I) as precursors. Suitable interconversions, such as alkylations, are well known to those skilled in the art and are described in many standard organic chemistry texts, such as 'Advanced Organic Chemistry' by Jerry March, fourth edition (Wiley, 1992), incorporated herein by reference. For example, compounds of formula (I) wherein $R^1$ is $C_{1-6}$alkyl, $C_{1-2}$alkyl substituted by one to five fluorine atoms, $C_{3-6}$alkenyl, $C_{3-6}$alkynyl, $C_{3-10}$cycloalkyl$C_{0-6}$alkyl, $C_{4-12}$bridged cycloalkyl, $A(CR^6R^7)_n$ (with the proviso that n is not zero) or $B(CR^6R^7)_n$ may be prepared by alkylating the corresponding compound of formula (I) wherein $R^1$ is H.

Acylation of compounds of formula (I) wherein $R^4$ is $NH_2$, to provide compounds of formula (I) wherein $R^4$ is $R^9$CONH, may be carried out by conventional means, for example by employing conventional acylating agents such as those described in 'Advanced Organic Chemistry', pp 417-424, incorporated herein by reference.

As will be appreciated by those skilled in the art it may be necessary or desirable at any stage in the synthesis of compounds of formula (I) to protect one or more sensitive groups in the molecule so as to prevent undesirable side reactions. The protecting groups used in the preparation of compounds of formula (I) may be used in conventional manner. See, for example, those described in 'Protective Groups in Organic Synthesis' by Theodora W. Greene and Peter G. M. Wuts, third edition, (Wiley, 1999), incorporated herein by reference, which also describes methods for the removal of such groups.

Amines and alcohols of formula (II) are either known compounds or may be prepared by literature methods, such as those described in 'Comprehensive Organic Transformations: a guide to functional group preparations' by Richard Larock (VCH, 1989), incorporated herein by reference.

Benzonitriles of formula (VI) are either known compounds or may be prepared by literature methods, such as that described by G. Atwell et al in *Anti-Cancer Drug Design* 1996, 11, 553, incorporated herein by reference. Where Y=N, nitriles of formula (VI) may be obtained by treating 5-bromo-2-pyridinecarbonitrile with a suitable nucleophile, such as sodium methanethiolate.

α,β-Unsaturated acids of formula (VII) are either known compounds or may be prepared by literature methods, such as that described by C. Kuroda et al in *Tetrahedron* 2000, 56, 6441, incorporated herein by reference.

Certain intermediates described above are novel compounds, and it is to be understood that all novel intermediates herein form further aspects of the present invention. Compounds of formulae (III) and (IV) are key intermediates and represent a particular aspect of the present invention.

Conveniently, compounds of the invention are isolated following work-up in the form of the free base. Pharmaceutically acceptable addition salts of the compounds of the invention may be prepared using conventional means.

Solvates (e.g. hydrates) of a compound of the invention may be formed during the work-up procedure of one of the aforementioned process steps.

The Intermediates and Examples that follow illustrate the invention but do not limit the invention in any way. All temperatures are in ° C. Silica chromatography refers to either flash column chromatography performed using Biotage column chromatography cartridges or Solid Phase Extraction (SPE) chromatography, using Varian Mega Bond Elut (Si) cartridges (Anachem) under 15 mmHg. Thin layer chromatography (Tlc) was carried out on silica plates. Nuclear magnetic resonance (NMR) spectra were recorded using a Bruker DPX400 spectrometer. Analytical HPLC was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 minutes 0% B, 0.7-4.2 minutes linear gradient to 100% B, 4.2-5.3 minutes 0% B, 5.3-5.5 minutes 0% B at a flow rate of 3 ml/minutes. The mass spectra (MS) were recorded on a Waters ZQ mass spectrometer using electrospray positive [(ES+ve to give MH+ and M(NH4)+ molecular ions] or electrospray negative [(ES−ve to give (M−H)— molecular ion] modes. Mass-directed preparative HPLC was conducted on a Supelco ABZ+ column (10 cm×10 mm ID, 5 μm) eluting with 0.1% $HCO_2H$ in water (solvent A), and 0.05% $HCO_2H$/5% water in acetonitrile (solvent B), using the following 10-minute elution gradients according to the LC retention time: 1.5-2.2 mins, 0-30% B; 2.0-2.8 mins, 5-30% B; 2.5-3.0 mins, 15-55% B; 2.8-4.0 mins, 30-80% B; 3.8-5.5 mins, 50-90% B. The mass spectra (MS) were recorded on a Micromass ZMD mass spectrometer using electrospray positive [(ES+ve to give MH+ and M(NH4)+ molecular ions] or electrospray negative [(ES−ve to give (M−H)— molecular ion] modes. In addition to those already defined, the following abbreviations are used: Me, methyl; NMP, N-methylpyrrolidinone; and THF, tetrahydrofuran.

Intermediate 1

4-Methyl-6-[4-(methylthio)phenyl]-2-pyridone

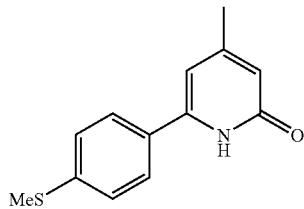

To a stirred solution of lithium diisopropylamide (50 mL of a 2M solution in heptane/THF/ethyl benzene, 0.1 mol) in THF (50 mL) at −78° C. and under an atmosphere of nitrogen was added dropwise a solution of 3-methyl-2-butenoic acid (5 g, 0.05 mol) in THF (50 mL). The reaction was warmed to 0° C. for 30 minutes. After cooling to −78° C., a solution of 4-(methylthio)benzonitrile (7.45 g, 0.05 mol) in THF (50 mL) was added dropwise. Upon complete addition, the reaction was warmed to room temperature and stirred for 3 hours. Water (150 mL) and ethyl acetate (100 mL) were added to the reaction mixture and the resulting precipitate filtered, washed with ethyl acetate and dried to give the title compound (4.96 g, 43%) LC retention time 2.75 mins, MS m/z 232 (MH$^+$).

Intermediate 2

4-Methyl-6-[4-(methylsulfonyl)phenyl]-2-pyridone

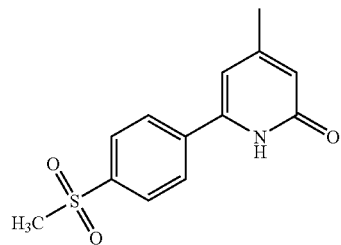

To a stirred mixture of intermediate 1 (3.7 g, 16.0 mmol) in methanol (150 mL) at 0° C. was added portionwise a suspension of Oxone™ (29.5 g, 48.0 mmol) in water (100 mL). The reaction was warmed to room temperature and stirred for 14 hours. The methanol was removed in vacuo and the resulting residue partitioned between saturated aqueous sodium bicarbonate (1 L) and chloroform (500 mL) and separated. The aqueous layer was further extracted with chloroform (3×200 mL) and the combined organic layers were dried over sodium sulfate, filtered and concentrated to give the title compound (3.20 g, 76%) LC retention time 2.20 mins, MS m/z 264 (MH$^+$).

Intermediate 3

4-Methyl-6-[4-(methylsulfonyl)phenyl]pyridine-2-trifluoromethanesulfonate

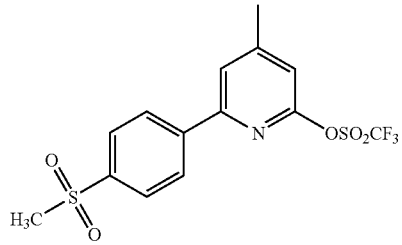

To a stirred solution of intermediate 2 (3.20 g, 12.2 mmol) in pyridine (150 mL) at 0° C. and under an atmosphere of nitrogen was added dropwise trifluoromethanesulfonic anhydride (2.46 mL, 14.6 mmol). After stirring for 1 hr at 0° C., the pyridine was removed in vacuo and the residue partitioned between water (200 mL) and dichloromethane (200 mL). The layers were separated and the aqueous phase further extracted with dichloromethane (3×100 mL). The combined organic layers were dried over sodium sulfate, filtered and concentrated in vacuo to give the title compound (4.27 g, 89%) LC retention time 3.48 mins, MS m/z 396 (MH$^+$).

EXAMPLE 1

N-Cyclopentyl-4-methyl-6-[4-(methylsulfonyl)phenyl]pyridine-2-amine

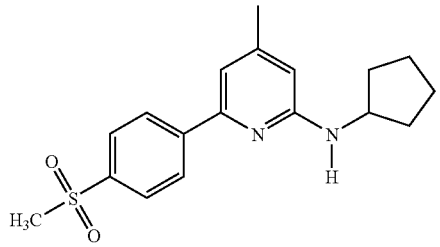

A stirred solution of intermediate 3 (60 mg, 0.15 mmol) and cyclopentylamine (60 μL, 0.76 mmol) in NMP (2 mL) was heated at 180° C. for 14 hours. Removal of the solvent (vacuum centrifuge) and purification by silica chromatography, eluting with a gradient of cyclohexane to ethyl acetate, gave the title compound (17 mg, TLC R$_F$ 0.45, 1:1 ethyl acetate:cyclohexane) MS m/z 331 (MH$^+$).

EXAMPLE 2

2-Benzyloxy-4-methyl-6-[4-(methylsulfonyl)phenyl]pyridine

Route A

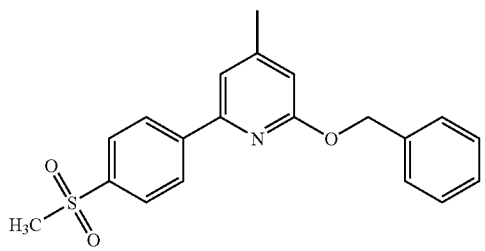

To a stirred solution of intermediate 2 (24 mg, 0.09 mmol) in DMF (0.5 mL) was added silver carbonate (28 mg, 0.10 mmol) followed by benzyl bromide (13 μL, 0.11 mmol). The reaction was stirred at room temperature in the dark for 14 h hours before being diluted with diethyl ether (5 mL), filtered, washed with water, dried over sodium sulfate, filtered and concentrated in vacuo to give the title compound (30 mg, 93%) LC retention time 3.54 mins, MS m/z 354 (MH$^+$).

Route B

To a stirred suspension of sodium hydride (9 mg, 0.22 mmol) in DMF (2 mL) at room temperature and under an atmosphere of nitrogen was added benzyl alcohol (0.02 mL, 0.19 mmol). After stirring for 1 hour, the reaction mixture was added to intermediate 3 (50 mg, 0.13 mmol) and the reaction heated at 250° C. with microwave irradiation. After cooling, the solvent was removed in vacuo and the residue partitioned between water (5 mL) and dichloromethane (5 mL). The layers were separated and the aqueous phase further extracted with dichloromethane (2×5 mL). The combined organic layers were dried over sodium sulfate, filtered, concentrated in vacuo and purified by silica chromatography eluting with a gradient of ethyl acetate in cyclohexane to give the title compound TLC R$_F$ 0.31 (1:3 ethyl acetate:cyclohexane) LC retention time 3.54 mins, MS m/z 354 (MH$^+$)

Intermediate 4

2-[4-(methylsulfonyl)phenyl]-4-methylpyridine

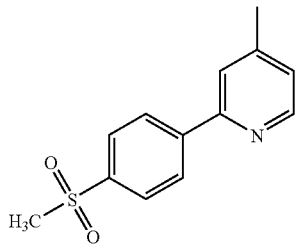

To a mixture of 2-chloro-4-methylpyridine (3 g, 23.5 mmol), 4-(methylsulfonyl)phenylboronic acid (5.64 g, 28.2 mmol), potassium phosphate (12.0 g, 56.4 mmol) and DMF (50 mL) under an atmosphere of nitrogen was added palladium tetrakistriphenylphosphine (1.36 g, 1.18 mmol). After heating at 120° C. for 14 hours, the reaction was cooled and the DMF removed in vacuo. The residue was partitioned between ethyl acetate (100 mL) and water (100 mL), separated and the organic layer dried over sodium sulfate and concentrated in vacuo. Purification by silica chromatography eluting with a gradient of ethyl acetate in cyclohexane gave the title compound (4.29 g, 74%) TLC R$_F$ 0.19 (1:1 ethyl acetate:cyclohexane) LC retention time 2.36 mins, MS m/z 248 (MH$^+$)

Intermediate 5

2-[4-(methylsulfonyl)phenyl]-4-methylpyridine-N-oxide

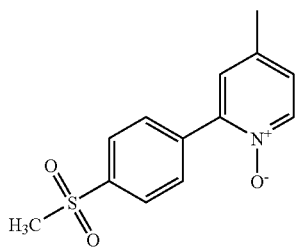

A solution of intermediate 4 (3 g, 12.2 mmol) in dichloromethane (5 mL) was added to a solution of 3-chloroperbenzoic acid (7.35 g of 57 to 86% grade material) in dichloromethane (15 mL) at reflux. After stirring for 3 hours at this temperature, the reaction was cooled, washed sequentially with saturated aqueous sodium bicarbonate solution, saturated aqueous sodium sulfite solution and water, dried over sodium sulfate and concentrated in vacuo to give the title compound (3.11 g, 97%) LC retention time 1.94 mins, MS m/z 264 (MH$^+$)

Intermediate 6

2-Chloro-4-methyl-6-[4-(methylsulfonyl)phenyl]pyridine

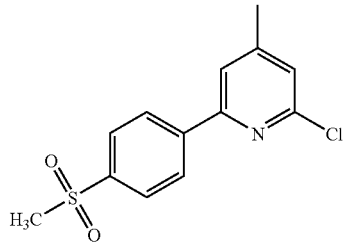

A mixture of intermediate 5 (3.11 g, 11.8 mmol) and phosphorus oxychloride (10 mL) was heated at 100° C. for 14 hours. After cooling, the reaction was quenched with saturated aqueous sodium bicarbonate solution, with cooling, extracted with dichloromethane and the combined organic extracts dried over sodium sulfate and concentrated in vacuo. Purification by silica chromatography eluting with a gradient of ethyl acetate in cyclohexane gave the title compound (1.91 g, 58%) TLC R$_F$ 0.35 (1:1 ethyl acetate:cyclohexane) LC retention time 3.13 mins, MS m/z 282 (MH$^+$)

EXAMPLE 3

N-Benzyl-N-methyl-4-methyl-6-[4-(methylsulfonyl)phenyl]pyridine-2-amine

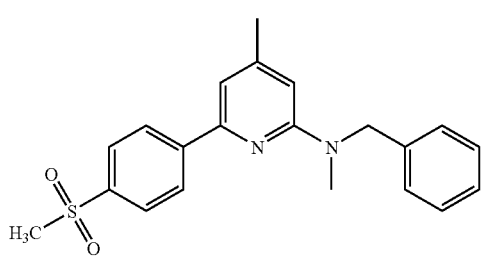

A solution of intermediate 6 (10 mg, 0.04 mmol) and N-methylbenzylamine (20 mg, 0.18 mmol) in NMP (0.5 mL) was heated at 250° C. in the microwave for 10 minutes. Removal of the solvent (vacuum centrifuge) and purification by silica chromatography, eluting with a gradient of cyclohexane to ethyl acetate, gave the title compound (5 mg) LC retention time 3.62 mins, MS m/z 367 (MH$^+$).

EXAMPLE 83

N-[(1-methyl-1H-pyrazol-4-yl)methyl]-4-methyl-6-[4-(methylsulfonyl)phenyl]pyridine-2-amine

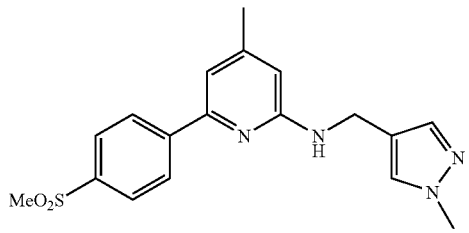

A stirred solution of intermediate 3 (1.25 g, 3.15 mmol) and (1-methyl-1H-pyrazol-4-yl)methylamine (0.70 g, 6.30 mmol) in NMP (10 mL) was heated at 180° C. for 14 hours, cooled, and loaded evenly onto 5 methanol-conditioned 10 g Varian bond-elut SCX-2 cartridge. The cartridges were washed with methanol (2×40 mL each) followed by a solution of 9:1 methanol/concentrated ammonium hydroxide (2×40 mL each). The ammoniacal fractions were concentrated and purified by silica chromatography eluting with a gradient of cyclohexane to ethyl acetate to give the title compound (780 mg) LC retention time 2.32 mins, MS m/z 357 (MH$^+$); $^1$H-NMR (CDCl$_3$) δ 2.23 (3H, s), 3.09 (3H, s), 3.88 (3H, s), 4.47 (2H, d, J=6 Hz), 4.68 (1H, br), 6.28 (1H, s), 6.99 (1H, s), 7.36 (1H, s), 7.50 (1H, s), 8.00 (2H, d, J=9 Hz), 8.19 (2H, d, J=9 Hz).

1-Ethyl-1H-1,2,4-triazole-5-carbaldehyde

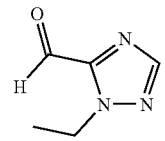

To a solution of 1-ethyl-1H-1,2,4-triazole (9.9 g, 0.10 mol) and N,N,N',N'-tetramethylethylenediamine (15 mL) in THF (60 mL) at −78° C. was added n-butyllithium (64 mL of a 1.6M solution in hexanes, 0.10 mol). After stirring for 2 hours, DMF (8.7 mL, 0.11 mol) was added, the reaction allowed to warm to room temperature and stirred for 14 hours before being poured into saturated aqueous sodium bicarbonate solution (300 mL). The mixture was extracted with dichloromethane (3×150 mL) and the combined organics dried over sodium sulfate, filtered and concentrated to give the title compound (>12 g) which also contained unreacted starting material $^1$H-NMR (CDCl$_3$) δ 1.48 (3H, t, J=7 Hz), 4.63 (2H, q, 7 Hz), 8.03 (1H, s), 10.04 (s, 1H).

1-Ethyl-1H-1,2,4-triazole-5-carbaldehyde oxime

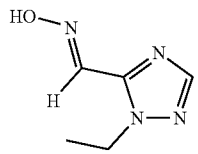

A mixture of crude 1-ethyl-1H-1,2,4-triazole-5-carbaldehyde (17.7 g), hydroxylamine hydrochloride (12.7 g, 0.182 mol), sodium bicarbonate (15.3 g, 0.182 mol) and ethanol (60 mL) was heated at reflux for 3 hours. After cooling, the reaction was filtered and the filtrate concentrated in vacuo. The resulting residue was crystallised from ethanol to give the title compound (6.17 g) $^1$H-NMR (d$_6$-DMSO) δ 1.32 (3H, t, J=7 Hz), 4.41 (2H, q, J=7 Hz), 8.02 (1H, s), 8.25 (1H, s), 12.70 (1H, s)

(1-Ethyl-1H-1,2,4-triazol-5-yl)methylammonium acetate

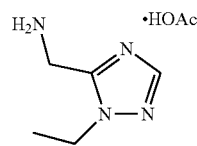

A mixture of 1-ethyl-1H-1,2,4-triazole-5-carbaldehyde oxime (6.17 g, 44 mmol), 10% palladium hydroxide on carbon (2.9 g) acetic acid (125 mL) and ethanol (125 mL) were stirred under an atmosphere of hydrogen for 14 hours. The reaction mixture was filtered and concentrated in vacuo to give the title compound (7.7 g) $^1$H-NMR (d$_6$-DMSO) δ 1.32 (3H, t, J=7 Hz), 1.89 (3H, s), 3.89 (2H, br), 4.17 (2H, q, J=7 Hz), 7.80 (1H, s).

EXAMPLE 234

N-[(1-ethyl-1H-1,2,4-triazol-5-yl)methyl]-4-methyl-6-[4-(methylsulfonyl)phenyl]pyridine-2-amine

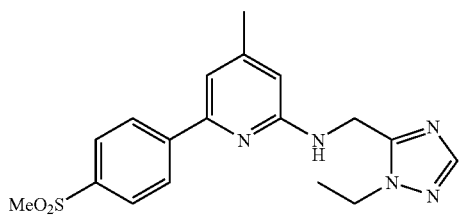

Portions of (1-ethyl-1H-1,2,4-triazol-5-yl)methylammonium acetate are conveniently converted to the free base (1-ethyl-1H-1,2,4-triazol-5-yl)methylamine by filtering a solution in methanol through an appropriate methanol-conditioned Varian bond-elut aminopropyl cartridge and concentrating the filtrate. A stirred solution of the free base (50 mg, 0.40 mmol) and intermediate 3 (63 mg, 0.16 mmol) in NMP (5 mL) was heated at 180° C. for 14 hours, cooled, and loaded onto a methanol-conditioned 10 g Varian bond-elut SCX-2 cartridge. The cartridges were washed with methanol (2×40 mL) followed by a solution of 9:1 methanol/concentrated ammonium hydroxide (2×40 mL). The ammoniacal fractions were concentrated and purified by mass-directed preparative HPLC to give the title compound (5 mg) LC retention time 2.61 mins, MS m/z 372 (MH$^+$); $^1$H-NMR (CDCl$_3$) δ 1.42 (3H, t, J=7 Hz), 2.32 (3H, s), 3.10 (3H, s), 4.27 (2H, q, J=7 Hz), 4.84 (2H, d, J=6 Hz), 5.17 (1H, t, J=6 Hz), 6.40 (1H, s), 7.00 (1H, s), 7.85 (1H, s), 8.00 (2H, d, J=9 Hz), 8.13 (2H, d, J=9 Hz).

Intermediate 7

2-[4-(methylthio)phenyl]-4-(trifluoromethyl)-pyridine

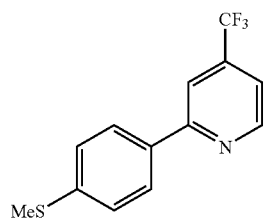

To a mixture of 2-chloro-4-(trifluoromethyl)pyridine (19.9 g, 0.11 mol), 4-(methylthio)phenylboronic acid (21.9 g, 0.13 mol), 1M aqueous sodium carbonate (180 mL) and 1,2-dimethoxyethane (270 mL) under an atmosphere of nitrogen was added palladium tetrakistriphenylphosphine (3.78 g, 3.3 mmol) and the reaction heated at 100° C. for 14 hours. After cooling and concentration in vacuo, the residue was partitioned between ethyl acetate (350 mL) and water (400 mL) and separated. The aqueous layer was further extracted with ethyl acetate (2×150 mL) and the combined organic layers were dried over sodium sulfate and concentrated in vacuo. Filtration through a pad of silica gel (200 g) eluting with a gradient of ethyl acetate in cyclohexane gave the title compound (29.4 g) LC retention time 3.62 mins, MS m/z 269 (MH$^+$).

Intermediate 8

2-[4-(methylsulfonyl)phenyl]-4-(trifluoromethyl)-pyridine

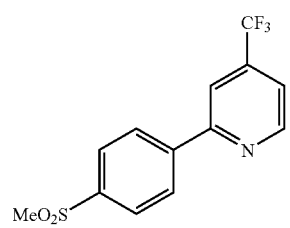

To a stirred suspension of intermediate 7 (29.4 g, 0.11 mol) in methanol (400 mL) at 0° C. was added portionwise a suspension of Oxone™ (134 g) in water (200 mL). The reaction was warmed to room temperature and stirred for 14 hours. The methanol was removed in vacuo and the residue diluted with saturated aqueous sodium bicarbonate (2 L) and extracted with ethyl acetate (3×1 L). The combined organic

Intermediate 9

2-Chloro-4-(trifluoromethyl)-6-[4-(methylsulfonyl)phenyl]pyridine

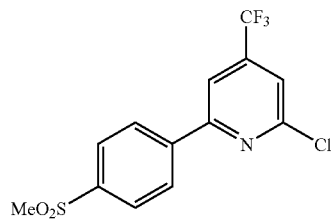

To a solution of intermediate 8 (32 g, 0.106 mol) in dichloromethane (400 mL) at reflux was added 3-chloroperbenzoic acid (41.7 g of 57 to 86% grade material) portionwise over 15 minutes. After stirring for 14 hours at reflux, the reaction was cooled, diluted with dichloromethane (2 L) and washed sequentially with saturated aqueous sodium bicarbonate solution, saturated aqueous sodium sulfite solution containing tetra-n-butylammonium sulfate (4 mL) and water, dried over sodium sulfate and concentrated in vacuo to give 2-[4-(methylsulfonyl)phenyl]-4-(trifluoromethyl)-pyridine-N-oxide (37.2 g, containing traces of a tetra-n-butylammonium salt) LC retention time 2.34, MS m/z 318 (MH$^+$). A mixture of this crude material and phosphorus oxychloride (110 mL) was heated at 110° C. for 4 hours. After cooling, the majority of the phosphorus oxychloride was removed in vacuo and the residue neutralised with saturated aqueous sodium bicarbonate solution (300 mL), with cooling. The mixture was extracted with chloroform and the combined organic extracts dried over sodium sulfate and concentrated in vacuo. The residue was recrystallised from 2-propanol to give the title compound (22.0 g) LC retention time 3.23 min, MS m/z 336/338 (MH$^+$).

EXAMPLE 54

N-cyclohexyl-4-(trifluoromethyl)-6-[4-(methylsulfonyl)phenyl]pyridine-2-amine

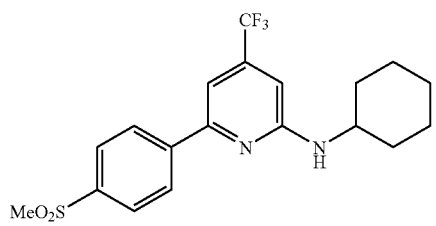

A stirred mixture of intermediate 9 (6 g, 17.8 mmol) and cyclohexylamine (175 mL) was heated at 110° C. for 14 hours. After cooling, the reaction was diluted with water (1 L), acidified with 2N HCl (750 mL) and filtered to give the title compound (6.48 g) LC retention time 3.81 mins MS m/z 399 (MH$^+$); $^1$H-NMR (CDCl$_3$) δ 1.22-1.86 (8H, m), 2.60-2.16 (2H, m), 3.09 (3H, s), 3.67-3.78 (1H, m), 4.84 (1H, d, J=7 Hz), 6.57 (1H, s), 7.19 (1H, s), 8.03 (2H, d, J=9 Hz), 8.17 (2H, d, J=9 Hz).

EXAMPLE 219

N-(cyclopentanemethyl)-4-(trifluoromethyl)-6-[4-(methylsulfonyl)phenyl]pyridine-2-amine

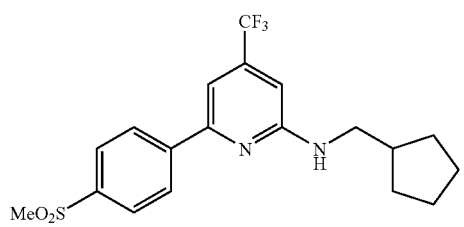

A stirred solution of intermediate 9 (630 mg, 1.9 mmol) and cyclopentanemethylamine (373 mg, 3.8 mmol) in NMP (5 mL) was heated at 180° C. for 14 hours. After cooling, the reaction was diluted with water (150 mL) and filtered to give the title product (582 mg) LC retention time 3.80 mins MS m/z 399 (MH$^+$); $^1$H-NMR (CDCl$_3$) δ 1.27-1.38 (2H, m), 1.52-1.74 (4H, m), 1.82-1.92 (2H, m) 2.23 (1H, hept, J=7 Hz), 3.10 (3H, s), 3.33 (2H, dd, J=7 Hz & 6 Hz), 4.95 (1H, t, J=6 Hz), 6.60 (1H, s), 7.22 (1H, s), 8.03 (2H, d, J=8 Hz), 8.19 (2H, d, J=8 Hz).

EXAMPLE 208

N-(2-pyridylmethyl)-4-trifluoromethyl-6-[4-(methylsulfonyl)phenyl]pyridine-2-amine

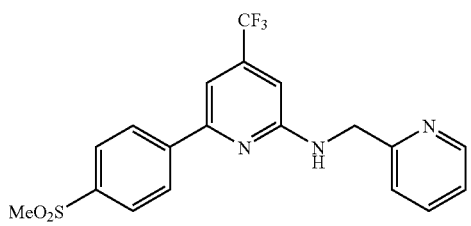

A solution of intermediate 9 (618 mg, 1.84 mmol) and 2-pyridylmethylamine (406 mg, 3.68 mmol) in NMP (4 mL) was heated at 250° C. with microwave irradiation for 10 minutes. The reaction was diluted with water (100 mL) and filtered to give a solid which was further purified by silica chromatography, eluting with a gradient of cyclohexane to ethyl acetate to give the title compound (471 mg) LC retention time 2.87 mins MS m/z 407 (MH$^+$); $^1$H-NMR (CDCl$_3$) δ 3.10 (3H, s), 4.81 (2H, d, J=5 Hz), 6.14 (1H, t, J=5 Hz), 6.76 (1H, s), 7.24 (1H, td, J=5 Hz & 2 Hz), 7.37 (1H, d, J=8 Hz), 7.71 (1H, td, J=8 Hz & 2 Hz), 8.03 (2H, d, J=8 Hz), 8.19 (2H, d, J=8 Hz), 8.62 (1H, d, J=5 Hz).

Intermediate 10

4-(Trifluoromethyl)-6-[4-(methylthio)phenyl]-2-pyridone

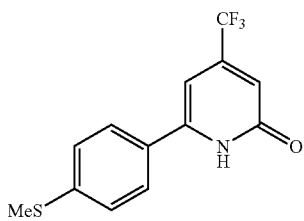

To a stirred solution of diisopropylamine (11.5 mL, 81.8 mmol) in THF (75 mL) at 0° C. was added n-butyllithium (51.1 mL of a 1.6M solution in hexanes, 81.8 mmol). After stirring for 15 minutes, a solution of 4,4,4-trifluoro-3-methyl-2-butenoic acid (6.0 g, 38.9 mmol) in THF (10 mL) was added dropwise. The reaction was allowed to warm to room temperature and stirred for 30 minutes before being cooled to 0° C. and treated dropwise with a solution of 4-(methylthio)benzonitrile (2.91 g, 19.5 mmol) in THF (10 mL). Upon complete addition, the reaction was heated at reflux for 14 hours. After cooling, water (200 mL) was added and the mixture extracted with ethyl acetate (250 mL). The organic phase was dried over sodium sulfate, filtered and concentrated in vacuo and the resulting residue purified by silica chromatography eluting with 1:1 ethyl acetate/cyclohexane to give the title product (2.43 g) LC retention time 3.10 mins MS m/z 286 (MH$^+$).

Intermediate 11

4-(Trifluoromethyl)-6-[4-(methylsulfonyl)phenyl]-2-pyridone

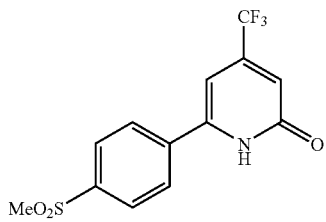

To a stirred mixture of intermediate 10 (2.43 g, 8.52 mmol) in methanol (100 mL) at 0° C. was added portionwise a suspension of Oxone™ (15.7 g, 25.6 mmol) in water (60 mL). The reaction was warmed to room temperature and stirred for 14 hours. The methanol was removed in vacuo and the resulting residue partitioned between saturated aqueous sodium bicarbonate (500 mL) and chloroform (200 mL) and separated. The aqueous layer was further extracted with chloroform (3×100 mL) and the combined organic layers were dried over sodium sulfate, filtered and concentrated to give the title compound (1.72 g) LC retention time 2.57 mins, MS m/z 318 (MH$^+$).

EXAMPLE 164

2-[4-(methylsulfonyl)phenyl]-6-[(2-pyridinylmethyl)oxy]-4-(trifluoromethyl)pyridine

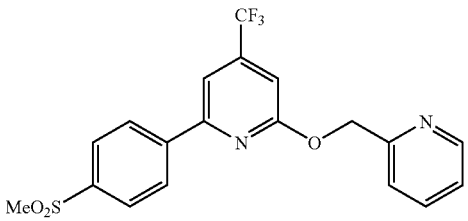

Diisopropylazodicarboxylate (0.93 mL, 4.7 mmol) was added dropwise to a solution of intermediate 11 (1 g, 3.2 mmol), 2-pyridinylmethanol (0.38 mL, 3.9 mmol) and triphenylphosphine (1.24 g, 4.7 mmol) in chloroform (80 mL). After stirring for 14 hours, the reaction was concentrated and the residue diluted with methanol and loaded onto a methanol-conditioned 10 g Varian bond-elut SCX-2 cartridge. The cartridge was washed with methanol (2×40 mL) followed by a solution of 9:1 methanol/2N hydrochloric acid. The combined acidic fractions were concentrated and the residue triturated with methanol to give the title compound as its hydrochloride salt (348 mg) LC retention time 3.35 mins, MS m/z 409 (MH$^+$); $^1$H-NMR (d$_6$-DMSO) δ 3.28 (3H, s), 5.79 (2H, s), 7.47 (1H, s), 7.64 (1H, t, J=6 Hz), 7.85 (1H, d, J=8 Hz), 8.03 (2H, d, J=9 Hz), 8.11 (1H, s), 8.17 (1H, t, J=8 Hz), 8.38 (2H, d, J=9 Hz), 8.75 (1H, d, J=6 Hz)

Intermediate 12

4-{[4-(methylthio)phenyl]carbonyl}morpholine

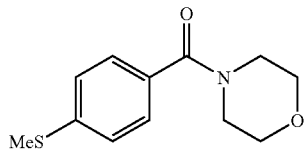

To a stirred solution of 4-(methylthio)benzoic acid (6.76 g, 40.2 mmol) and N-[2-(dimethylamino)ethyl]-N'-ethylcarbodiimide hydrochloride (9.24 g, 48.2 mmol) in THF (100 mL) was added morpholine (4.2 mL, 48.2 mmol). After stirring for 2 hours, the reaction was concentrated in vacuo and the residue partitioned between ethyl acetate (100 mL) and 2M hydrochloric acid (150 mL). The organic phase was separated, washed with 1M aqueous sodium carbonate solution, dried over sodium sulfate, filtered and concentrated in vacuo to give the title compound LC retention time 3.52 mins MS m/z 238 (MH$^+$).

Intermediate 13

1-[4-(methylthio)phenyl]-2-pentyn-1-one

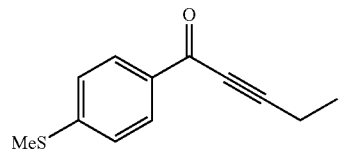

To a stirred solution of 1-butyne (approximately 4 g) in THF (50 mL) at −78° C. was added dropwise n-butyllithium (47 mL of a 1.6M solution in hexanes). Upon complete addition the reaction was allowed to warm to room temperature and stirred for a further 15 minutes. To the reaction was then added a solution of intermediate 12 (5.97 g) in THF (40 mL). After stirring for 45 minutes, the reaction was added to a 2:1 mixture of acetic acid and water (150 mL) at 0° C. Diethyl ether (50 mL) was added and the organic phase separated, washed with saturated aqueous sodium chloride solution, dried over sodium sulfate, filtered and concentrated in vacuo to give the title compound (5.09 g) LC retention time 3.37 mins MS m/z 205 (MH+).

Intermediate 14

Ethyl 4-ethyl-2-oxo-6-[4-(methylthio)phenyl]-2H-pyran-3-carboxylate

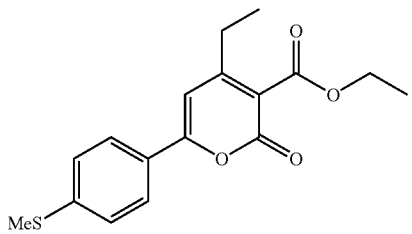

To a stirred solution of sodium ethoxide (0.95 g, 13.9 mmol) in ethanol (50 mL) was added diethyl malonate (10.7 mL, 69.4 mmol). After stirring for 30 minutes, a solution of intermediate 13 (2.84 g, 13.9 mmol) in ethanol (50 mL) was added and the reaction heated to reflux for 2 hours. After cooling (ice bath), the reaction was acidified to pH ~1 using 2M hydrochloric acid and partitioned between diethyl ether (200 mL) and water (50 mL). The aqueous phase was further extracted with diethyl ether (2×200 mL) and the combined organic phases were dried over sodium sulfate, filtered and concentrated in vacuo. The resulting crude product was purified by silica chromatography, eluting with a gradient of cyclohexane to ethyl acetate to give the title compound (3.33 g) LC retention time 3.47 mins MS m/z 319 (MH+).

Intermediate 15

4-Ethyl-6-[4-(methylthio)phenyl]-2(1H)-pyridone

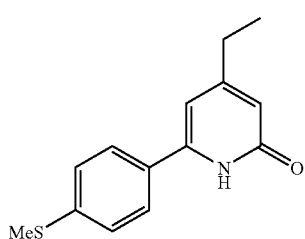

A mixture of intermediate 14 (3.33 g, 10.5 mmol), concentrated ammonium hydroxide solution (20 mL) and 1,4-dioxane (40 mL) were heated at 70° C. in a sealed vessel for 14 hours. After cooling, the reaction was concentrated to a residue which was triturated with methanol to give the title compound (2.03 g) LC retention time 2.87 mins MS m/z 246 (MH+).

Intermediate 16

4-Ethyl-6-[4-(methylsulfonyl)phenyl]-2(1H)-pyridone

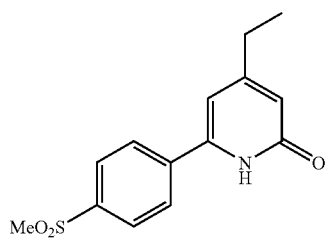

To a stirred mixture of intermediate 15 (2.0 g, 8.15 mmol) in methanol (60 mL) at 0° C. was added portionwise a suspension of Oxone™ (15.0 g, 24.5 mmol) in water (80 mL). The reaction was warmed to room temperature and stirred for 14 hours. The methanol was removed in vacuo and the resulting residue partitioned between saturated aqueous sodium bicarbonate (100 mL) and chloroform (100 mL) and separated. The aqueous layer was further extracted with chloroform (3×50 mL) and the combined organic layers were dried over sodium sulfate, filtered and concentrated to give the title compound (1.98 g) LC retention time 2.33 mins, MS m/z 278 (MH+).

Intermediate 17

4-Ethyl-6-[4-(methylsulfonyl)phenyl]pyridine-2-trifluoromethanesulfonate

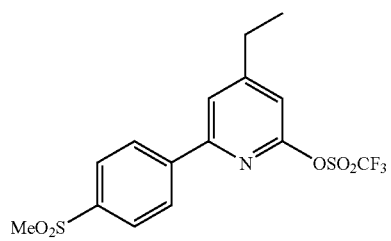

To a stirred solution of intermediate 16 (1.98 g, 7.14 mmol) in pyridine (80 mL) at 0° C. and under an atmosphere of nitrogen was added dropwise trifluoromethanesulfonic anhydride (1.44 mL, 8.57 mmol), and the reaction was allowed to warm to room temperature. After stirring for 14 hours, the pyridine was removed in vacuo and the residue partitioned between water (100 mL) and dichloromethane (100 mL). The layers were separated and the aqueous phase further extracted with dichloromethane (3×50 mL). The combined organic layers were dried over sodium sulfate, filtered and concentrated in vacuo to give the title compound (2.70 g) LC retention time 3.52 mins, MS m/z 410 (MH+).

EXAMPLE 89
4-Ethyl-6-[4-(methylsulfonyl)phenyl]-N-(tetrahydro-2H-pyran-4-yl)pyridine-2-amine

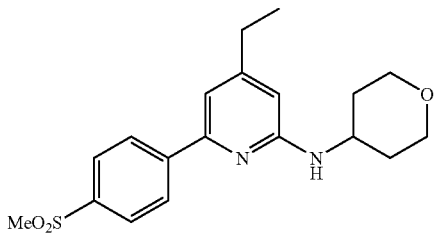

A stirred solution of intermediate 17 (41 mg, 0.10 mmol) and tetrahydro-2H-pyran-4-ylamine (21 mg, 0.20 mmol) in NMP (1 mL) was heated at 180° C. for 14 hours. After cooling, the reaction was loaded onto a methanol-conditioned 10 g Varian bond-elut SCX-2 cartridge. The cartridges were washed with methanol (2×40 mL) followed by a solution of 9:1 methanol/concentrated ammonium hydroxide (2×40 mL). The ammoniacal fractions were concentrated and purified by silica chromatography eluting with a gradient of cyclohexane to ethyl acetate to give the title compound (29 mg) LC retention time 2.78 mins, MS m/z 361 (MH$^+$); $^1$H-NMR (CDCl$_3$) δ 1.27 (3H, t, J=8 Hz), 1.57 (2H, qd, J=11 Hz & 4 Hz), 2.11 (2H, d, J=10 Hz), 2.62 (2H, q, J=8 Hz), 3.08 (3H, s), 3.58 (2H, t, J=10 Hz), 3.94-4.08 (3H, m), 4.50 (1H, br s), 6.27 (1H, s), 6.96 (1H, s), 7.99 (2H, d, J=8 Hz), 8.14 (2H, d, J=8 Hz)

Intermediate 18
3-Chloro-4-ethyl-6-[4-(methylsulfonyl)phenyl]-2(1H)-pyridinone

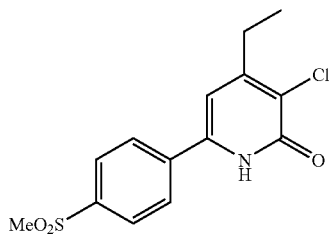

To a stirred solution of intermediate 16 (200 mg, 0.72 mmol) in acetic acid (5 mL) was added N-chlorosuccinimide (96 mg, 0.72 mmol) and the reaction heated at 90° C. for 4 hours. After cooling, the reaction was concentrated in vacuo and partitioned between water (25 mL) and 4:1 Chloroform/2-propanol (50 mL). The organic phase was dried over sodium sulfate, filtered and concentrated in vacuo to give the crude title compound (>200 mg) LC retention time 2.54 mins MS m/z 312/314 (MH$^+$).

EXAMPLE 220
3-Chloro-4-ethyl-6-[4-(methylsulfonyl phenyl]-2-[(2-pyridinylmethyl)oxy]pyridine

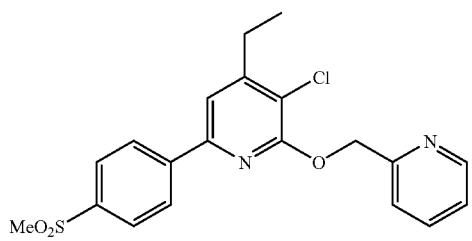

Diisopropylazodicarboxylate (0.076 mL, 0.39 mmol) was added dropwise to a solution of intermediate 18 (80 mg, 0.26 mmol), 2-pyridinylmethanol (0.031 mL, 0.32 mmol) and triphenylphosphine (101 mg, 0.39 mmol) in chloroform (4 mL). After stirring for 14 hours, the reaction was concentrated and the residue diluted with methanol and loaded onto a methanol-conditioned 10 g Varian bond-elut SCX-2 cartridge. The cartridge was washed with methanol (2×40 mL) followed by a solution of 9:1 methanol/concentrated ammonium hydroxide (2×40 mL). The ammoniacal fractions were concentrated and purified by mass-directed preparative HPLC to give the title compound (41 mg) LC retention time 3.35 mins MS m/z 403/405 (MH$^+$); $^1$H-NMR (CDCl$_3$) δ 1.32 (3H, t, J=8 Hz), 2.87 (2H, q, J=8 Hz), 3.09 (3H, s), 5.70 (2H, s), 7.24 (1H, dd, J=7 Hz & 5 Hz), 7.36 (1H, s), 7.60 (1H, d, J=8 Hz), 7.74 (1H, td, J=8 Hz & 2 Hz), 7.99 (2H, d, J=8 Hz), 8.14 (2H, d, J=8 Hz), 8.63 (1H, d, J=5 Hz).

Intermediate 19
1-[4-(Methylsulfonyl)phenyl]-2-pentyn-1-one

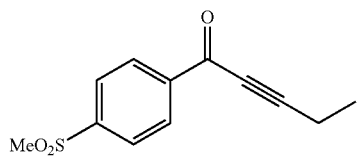

To a stirred mixture of intermediate 13 (2.0 g, 9.79 mmol) in acetonitrile (75 mL) at 0° C. was added portionwise a suspension of Oxone™ (13.2 g, 21.5 mmol) in water (75 mL). The reaction was warmed to room temperature and stirred for 14 hours. The methanol was removed in vacuo and the resulting residue partitioned between water (100 mL) and ethyl acetate (100 mL) and separated. The organic phase was dried over sodium sulfate, filtered and concentrated to give the title compound (2.24 g) LC retention time 2.76 mins, MS m/z 237 (MH$^+$).

Intermediate 20
4-Ethyl-6-[4-(methylsulfonyl)phenyl]-2-oxo-1,2-dihydro-3-pyridinecarbonitrile

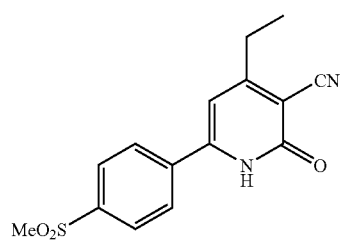

To a stirred solution of sodium ethoxide (645 mg, 9.5 mmol) in ethanol (40 mL) was added cyanoacetamide (1.59 g, 19.0 mmol). After stirring for 15 minutes, a solution of intermediate 19 (2.24 g, 9.5 mmol) in ethanol (20 mL) was added. Stirring was continued for a further 5 hours, at which time the reaction was made acidic with 2M hydrochloric acid. Water (100 mL) was added and the suspension filtered to give the title compound (1.54 g) LC retention time 2.42 mins MS m/z 303 (MH$^+$).

EXAMPLE 236

4-Ethyl-2-{[(6-methyl-3-pyridinyl)methyl]oxy}-6-[4-(methylsulfonyl)phenyl]-3-pyridinecarbonitrile

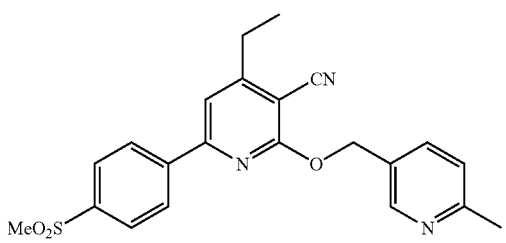

Diisopropylazodicarboxylate (0.049 mL, 0.25 mmol) was added dropwise to a solution of intermediate 20 (50 mg, 0.17 mmol), (6-methyl-3-pyridinyl)methanol (0.023 mL, 0.21 mmol) and triphenylphosphine (65 mg, 0.25 mmol) in chloroform (2 mL). After stirring for 14 hours, the reaction was diluted with chloroform (10 mL), washed with water (10 mL), concentrated and the residue triturated with diethyl ether to give the title compound (35 mg) LC retention time 2.81 mins MS m/z 408 (MH$^+$); $^1$H-NMR (d$_6$-DMSO) δ 1.29 (3H, t, J=8 Hz), 2.46 (3H, s), 2.85 (2H, q, J=8 Hz), 3.30 (3H, s), 5.64 (2H, s), 7.31 (1H, d, J=8 Hz), 7.84 (1H, dd, J=8 Hz & 2 Hz), 7.92 (1H, s), 8.08 (2H, d, J=8 Hz), 8.45 (2H, d, J=8 Hz), 8.63 (1H, d, 2 Hz).

Intermediate 21

3-Cyano-4-ethyl-6-[4-(methylsulfonyl)phenyl]-2-pyridinyl trifluoromethanesulfonate

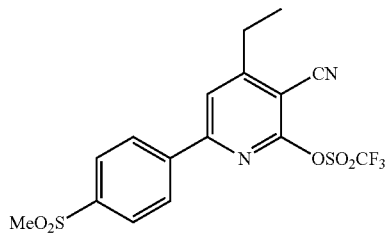

To a stirred solution of intermediate 20 (845 mg, 2.79 mmol) in pyridine (10 mL) at 0° C. and under an atmosphere of nitrogen was added dropwise trifluoromethanesulfonic anhydride (0.71 mL, 4.19 mmol), and the reaction was allowed to warm to room temperature. After stirring for 14 hours, the pyridine was removed in vacuo and the residue partitioned between water (100 mL) and dichloromethane (100 mL). The layers were separated and the aqueous phase further extracted with dichloromethane (3×50 mL). The combined organic layers were dried over sodium sulfate, filtered and concentrated in vacuo and the resulting residue purified by silica chromatography eluting with a gradient of cyclohexane to ethyl acetate to give the title compound (1.10 g) LC retention time 3.54 mins, MS m/z 435 (MH$^+$).

EXAMPLE 222

4-Ethyl-6-[4-(methylsulfonyl)phenyl]-2-[(2-pyridinylmethyl)amino]-3-pyridinecarbonitrile

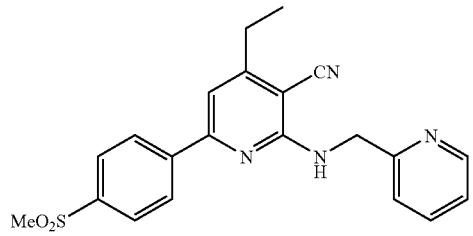

A stirred solution of intermediate 21 (80 mg, 0.18 mmol) and 2-pyridinylmethylamine (0.038 mL, 0.37 mmol) in NMP (1 mL) was stirred at room temperature for 14 hours. The reaction was filtered through a methanol-conditioned 5 g Varian bond-elut aminopropyl cartridge onto a methanol-conditioned 5 g Varian bond-elut SCX-2 cartridge. The SCX-2 cartridge was washed with methanol (2×20 mL) followed by a solution of 9:1 methanol/concentrated ammonium hydroxide (2×20 mL). The ammoniacal fractions were concentrated and the residue triturated with diethyl ether to give the title compound (25 mg) LC retention time 2.83 mins, MS m/z 393 (MH$^+$); $^1$H-NMR (d$_6$-DMSO) δ 1.27 (3H, t, J=8 Hz), 2.76 (2H, q, J=8 Hz), 3.24 (3H, s), 4.77 (2H, d, J=6 Hz), 7.24 (1H, dd, J=7 Hz & 5 Hz), 7.35 (1H, d, J=8 Hz), 7.37 (1H, s), 7.73 (1H, td, J=8 Hz & 2 Hz), 7.85 (1H, t, J=5 Hz), 7.95 (2H, d, J=9 Hz), 8.15 (2H, d, J=9 Hz), 8.55 (1H, d, J=5 Hz).

EXAMPLES 4 TO 236

Examples 4 to 236, as shown in Tables 1 to 5 that follow, were prepared in the manner described for Examples 1 to 3, 83, 234, 54, 219, 208, 164, 89, 220, 236 and 222 as appropriate.

TABLE 1

(I)

| Ex | R$^1$ | X | R$^3$ | R$^5$ | Y | MS |
|---|---|---|---|---|---|---|
| 4 | 4-chlorobenzyl | NH | CH$_3$ | H | C | MH+ 387 |
| 5 | benzyl | NCH$_3$ | CF$_3$ | H | C | MH+ 421 |

TABLE 1-continued

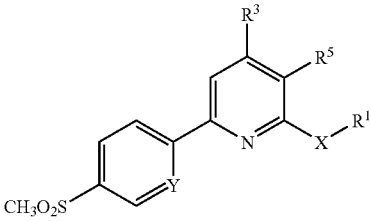

(I)

| Ex | R¹ | X | R³ | R⁵ | Y | MS | |
|---|---|---|---|---|---|---|---|
| 6 | 2-furylmethyl | NH | CF₃ | H | C | MH+ | 397 |
| 7 | benzyl | NH | CH₃ | H | C | MH+ | 353 |
| 8 | cyclohexanemethyl | NH | CF₃ | H | C | MH+ | 413 |
| 9 | 4-methoxyphenyl | NH | CH₃ | H | C | MH+ | 369 |
| 10 | 2-methylpropyl | O | CH₃ | H | C | MH+ | 320 |
| 11 | 3-pyridyl | O | CH₃ | H | C | MH+ | 341 |
| 12 | allyl | NH | CF₃ | H | C | MH+ | 357 |
| 13 | 2-chlorophenyl | NH | CH₃ | H | C | MH+ | 373 |
| 14 | 3,5-difluorobenzyl | NH | CH₃ | H | C | MH+ | 389 |
| 15 | 3-pyridinemethyl | NH | CH₃ | H | C | MH+ | 354 |
| 16 | 4-methoxyphenyl | NH | CF₃ | H | C | MH+ | 423 |
| 17 | cyclohexyl | NH | CH₃ | H | C | MH+ | 345 |
| 18 | n-butyl | NH | CF₃ | H | C | MH+ | 373 |
| 19 | 2-methylpropyl | NH | CF₃ | H | C | MH+ | 373 |
| 20 | 4-methoxybenzyl | NH | CH₃ | H | C | MH+ | 383 |
| 21 | 4-fluorobenzyl | NH | CH₃ | H | C | MH+ | 371 |
| 22 | 2-(5-methylfuryl)methyl | NH | CF₃ | H | C | MH+ | 411 |
| 23 | n-butyl | NH | CH₃ | H | C | MH+ | 319 |
| 24 | 2-furylmethyl | NH | CH₃ | H | C | MH+ | 343 |
| 25 | 4-methylbenzyl | NH | CH₃ | H | C | MH+ | 367 |
| 26 | cyclopentyl | NH | CF₃ | H | C | MH+ | 385 |
| 27 | 4-pyridinemethyl | NH | CH₃ | H | C | MH+ | 354 |
| 28 | 2-pyridinemethyl | NH | CH₃ | H | C | MH+ | 354 |
| 29 | 2-(6-methylpyridine)methyl | NH | CH₃ | H | C | MH+ | 382 |
| 30 | 4-ethoxybenzyl | NH | CH₃ | H | C | MH+ | 397 |
| 31 | 2-methylpropyl | NH | CH₃ | H | C | MH+ | 319 |
| 32 | propargyl | NH | CF₃ | H | C | MH+ | 355 |
| 33 | cyclohexanemethyl | NH | CH₃ | H | C | MH+ | 359 |
| 34 | 4-pyranylmethyl | NH | CH₃ | H | C | MH+ | 361 |
| 35 | 2-tetrahydrofurylmethyl | NH | CH₃ | H | C | MH+ | 347 |
| 36 | 2,2-dimethylpropyl | NH | CH₃ | H | C | MH+ | 333 |
| 37 | 2,2,2-trifluoroethyl | NH | CH₃ | H | C | MH+ | 345 |
| 38 | n-butyl | NCH₃ | CH₃ | H | C | MH+ | 333 |
| 39 | ethyl | NEt | CH₃ | H | C | MH+ | 319 |
| 40 | benzyl | NH | CF₃ | H | C | MH+ | 407 |
| 41 | 4-methylphenyl | NH | CH₃ | H | C | MH+ | 353 |
| 42 | 2-furylmethyl | NH | CH₃ | H | C | MH+ | 343 |
| 43 | 4-fluorophenyl | NH | CH₃ | H | C | MH+ | 357 |
| 44 | 2-thiophenylmethyl | NH | CH₃ | H | C | MH+ | 359 |
| 45 | benzyl | NCH₃ | C₂H₅ | H | C | MH+ | 381 |
| 46 | 4-pyranylmethyl | NH | C₂H₅ | H | C | MH+ | 375 |
| 47 | 2-methylpropyl | NH | C₂H₅ | H | C | MH+ | 333 |
| 48 | 4-methylbenzyl | NH | CF₃ | H | C | MH+ | 421 |
| 49 | 2-methylbenzyl | NH | CF₃ | H | C | MH+ | 421 |
| 50 | 2-chlorobenzyl | NH | CF₃ | H | C | MH+ | 441 |
| 51 | 2-(5-methylpyrazine)methyl | NH | CF₃ | H | C | MH+ | 423 |
| 52 | (S)-α-methylbenzyl | NH | CF₃ | H | C | MH+ | 421 |
| 53 | (R)-α-methylbenzyl | NH | CF₃ | H | C | MH+ | 421 |
| 54 | cyclohexyl | NH | CF₃ | H | C | MH+ | 399 |
| 55 | 4-methoxybenzyl | NH | CF₃ | H | C | MH+ | 437 |
| 56 | 6-methylpyridin-3-yl | NH | CH₃ | H | C | MH+ | 354 |
| 57 | benzyl | NH | H | CH₃ | C | MH+ | 353 |
| 58 | benzyl | NCH₃ | CH₃ | CH₃ | C | MH+ | 381 |
| 59 | benzyl | NH | CH₃ | CH₃ | C | MH+ | 367 |
| 60 | 2-methylpropyl | NH | CH₃ | CH₃ | C | MH+ | 333 |
| 61 | benzyl | NCH₃ | H | H | C | MH+ | 353 |
| 62 | benzyl | NCH₃ | CH₃ | H | N | MH+ | 368 |
| 63 | 4-methoxybenzyl | NH | CH₃ | H | N | MH+ | 370 |
| 64 | 2-methoxyethyl | NH | CH₃ | H | C | MH+ | 321 |
| 68 | 2-(6-methylpyridine)methyl | NCH₃ | CH₃ | H | C | MH+ | 382 |
| 69 | 2-furylmethyl | NH | C₂H₅ | H | C | MH+ | 357 |
| 70 | 4-methoxyphenyl | NH | CH₃ | H | N | MH+ | 370 |
| 71 | 1-methylethyl | NH | CH₃ | H | C | MH+ | 305 |
| 74 | 1-ethylpropyl | NH | CH₃ | H | C | MH+ | 333 |
| 75 | benzyl | NH | H | H | C | MH+ | 339 |

TABLE 1-continued

Structure (I): A pyridine core with R³ at position 4, R⁵ at position 3, X-R¹ at position 2, and position 6 connected to a phenyl ring bearing CH₃O₂S group; Y is a ring atom in the phenyl ring.

| Ex | R¹ | X | R³ | R⁵ | Y | MS | |
|---|---|---|---|---|---|---|---|
| 76 | 1H-imidazol-2-ylmethyl | NH | $CH_3$ | H | C | MH+ | 343 |
| 77 | 1H-pyrazol-4-ylmethyl | NH | $CH_3$ | H | C | MH+ | 343 |
| 80 | (1-methyl-1H-imidazol-2-yl)methyl | NH | $CH_3$ | H | C | MH+ | 357 |
| 81 | (3-methyl-1H-pyrazol-4-yl)methyl | NH | $CH_3$ | H | C | MH+ | 357 |
| 82 | (1-methyl-1H-pyrazol-3-yl)methyl | NH | $CH_3$ | H | C | MH+ | 357 |
| 84 | 1H-imidazol-2-ylmethyl | NH | $C_2H_5$ | H | C | MH+ | 357 |
| 85 | (3-methyl-1H-pyrazol-5-yl)methyl | O | $CH_3$ | H | C | MH+ | 358 |
| 86 | (1-methyl-1H-pyrazol-5-yl)methyl | O | $CH_3$ | H | C | MH+ | 358 |
| 87 | (1-methyl-1H-1,2,4-triazol-5-yl)methyl | NH | $CH_3$ | H | C | MH+ | 358 |
| 88 | (5-methyl-3-isoxazolyl)methyl | O | $CH_3$ | H | C | MH+ | 359 |
| 92 | cyclohexyl | NH | $CH_2F$ | H | C | MH+ | 363 |
| 93 | benzyl | NH | $C_2H_5$ | H | C | MH+ | 367 |
| 94 | (S)-α-methylbenzyl | NH | $CH_3$ | H | C | MH+ | 367 |
| 95 | 2-methylbenzyl | NH | $CH_3$ | H | C | MH+ | 367 |
| 96 | benzyl | O | $C_2H_5$ | H | C | MH+ | 368 |
| 97 | benzyl | $NCH_3$ | $CH_3$ | H | C | MH+ | 368 |
| 98 | (6-methyl-3-pyridyl)methyl | NH | $CH_3$ | H | C | MH+ | 368 |
| 99 | 6-methylpyridin-3-yl | NH | $C_2H_5$ | H | C | MH+ | 368 |
| 100 | benzyl | NH | $C_2H_5$ | H | C | MH+ | 368 |
| 101 | 3-pyridylmethyl | O | $C_2H_5$ | H | C | MH+ | 369 |
| 103 | 2-pyrazinylmethyl | NH | $C_2H_5$ | H | C | MH+ | 369 |
| 104 | benzyl | NH | $CH_2F$ | H | C | MH+ | 371 |
| 105 | 4-fluorophenyl | NH | $C_2H_5$ | H | C | MH+ | 371 |
| 106 | 2-(5-methylfuryl)methyl | NH | $C_2H_5$ | H | C | MH+ | 371 |
| 107 | (2-methyl-1H-imidazol-4-yl)methyl | NH | $C_2H_5$ | H | C | MH+ | 371 |
| 108 | (1-methyl-1H-imidazol-2-yl)methyl | NH | $C_2H_5$ | H | C | MH+ | 371 |
| 109 | (4-methyl-1H-imidazol-5-yl)methyl | NH | $C_2H_5$ | H | C | MH+ | 371 |
| 110 | (1-methyl-1H-imidazol-2-yl)methyl | $NCH_3$ | $CH_3$ | H | C | MH+ | 371 |
| 111 | (4-methyl-1H-imidazol-2-yl)methyl | NH | $C_2H_5$ | H | C | MH+ | 371 |
| 112 | (1-ethyl-1H-imidazol-2-yl)methyl | NH | $CH_3$ | H | C | MH+ | 371 |
| 113 | (1,3-dimethyl-1H-pyrazol-4-yl)methyl | NH | $CH_3$ | H | C | MH+ | 371 |
| 114 | (1,5-dimethyl-1H-pyrazol-4-yl)methyl | NH | $CH_3$ | H | C | MH+ | 371 |
| 115 | (1-methyl-1H-pyrazol-4-yl)methyl | NH | $C_2H_5$ | H | C | MH+ | 371 |
| 116 | (1-methyl-1H-pyrazol-5-yl)methyl | O | $C_2H_5$ | H | C | MH+ | 372 |
| 120 | 2-thiophenylmethyl | NH | $C_2H_5$ | H | C | MH+ | 373 |
| 121 | cyclohexyl | $NC_2H_5$ | $CH_3$ | H | C | MH+ | 373 |
| 123 | (3-methyl-5-isothiazolyl)methyl | NH | $CH_3$ | H | C | MH+ | 374 |
| 124 | (4-methyl-1,3-thiazol-2-yl)methyl | NH | $CH_3$ | H | C | MH+ | 374 |
| 125 | (3-methyl-4-isothiazolyl)methyl | NH | $CH_3$ | H | C | MH+ | 374 |
| 126 | [1-(fluoromethyl)-1H-pyrazol-4-yl]methyl | NH | $CH_3$ | H | C | MH+ | 375 |
| 128 | benzyl | $NC_2H_5$ | $CH_3$ | H | C | MH+ | 381 |
| 129 | 4-methylbenzyl | NH | $C_2H_5$ | H | C | MH+ | 381 |
| 131 | (1-methyl-1H-pyrazol-4-yl)methyl | NH | $CH_3$ | CN | C | MH+ | 382 |

TABLE 1-continued

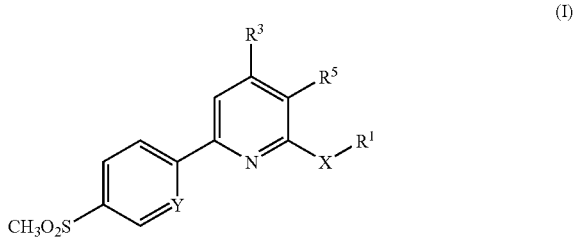

(I)

| Ex | R¹ | X | R³ | R⁵ | Y | MS | |
|---|---|---|---|---|---|---|---|
| 132 | 2-(6-methylpyridine)methyl | NH | $C_2H_5$ | H | C | MH+ | 382 |
| 133 | (2-methyl-3-pyridyl)methyl | O | $C_2H_5$ | H | C | MH+ | 383 |
| 134 | (6-methyl-3-pyridyl)methyl | O | $C_2H_5$ | H | C | MH+ | 383 |
| 135 | 2-(6-methylpyridine)methyl | O | $C_2H_5$ | H | C | MH+ | 383 |
| 137 | (1-methyl-1H-imidazol-2-yl)methyl | NH | $C_2H_5$ | H | C | MH+ | 385 |
| 138 | (1,3-dimethyl-1H-pyrazol-4-yl)methyl | NH | $CH_3$ | H | C | MH+ | 385 |
| 139 | (1,5-dimethyl-1H-pyrazol-4-yl)methyl | NH | $C_2H_5$ | H | C | MH+ | 385 |
| 142 | (4-methyl-1,3-thiazol-2-yl)methyl | NH | $C_2H_5$ | H | C | MH+ | 388 |
| 143 | (1-methyl-1H-pyrazol-4-yl)methyl | NH | $C_2H_5$ | F | C | MH+ | 389 |
| 144 | [1-(fluoromethyl)-1H-pyrazol-4-yl]methyl | NH | $C_2H_5$ | H | C | MH+ | 389 |
| 147 | (1-methyl-1H-pyrazol-4-yl)methyl | NH | $CH_3$ | Cl | C | MH+ | 391/393 |
| 148 | benzyl | NH | $C_2H_5$ | CN | C | MH+ | 392 |
| 149 | (6-methyl-3-pyridyl)methyl | O | $CH_3$ | CN | C | MH+ | 394 |
| 150 | 3-pyridyl | O | $CF_3$ | H | C | MH+ | 395 |
| 151 | benzyl | NH | $C(CH_3)_3$ | H | C | MH+ | 395 |
| 152 | 2-(6-methylpyridine)methyl | $NCH_3$ | $C_2H_5$ | H | C | MH+ | 396 |
| 153 | 1H-imidazol-2-ylmethyl | NH | $CF_3$ | H | C | MH+ | 397 |
| 154 | 4-ethoxyphenyl | NH | $C_2H_5$ | H | C | MH+ | 397 |
| 155 | tetrahydro-2H-pyran-4-yl | NH | $CF_3$ | H | C | MH+ | 401 |
| 158 | (6-methyl-3-pyridyl)methyl | O | $CH_3$ | H | C | MH+ | 369 |
| 160 | 2-methyl-3-pyridyl | NH | $CF_3$ | H | C | MH+ | 408 |
| 162 | 6-methyl-2-pyridyl | NH | $CF_3$ | H | C | MH+ | 408 |
| 163 | 6-methylpyridin-3-yl | NH | $CF_3$ | H | C | MH+ | 408 |
| 165 | 2-methyl-3-pyridyl | O | $CF_3$ | H | C | MH+ | 409 |
| 166 | 3-pyridylmethyl | O | $CF_3$ | H | C | MH+ | 409 |
| 167 | 6-methylpyridin-3-yl | O | $CF_3$ | H | C | MH+ | 409 |
| 168 | 2-pyrazinylmethyl | NH | $CF_3$ | H | C | MH+ | 409 |
| 169 | 4-fluorophenyl | NH | $CF_3$ | H | C | MH+ | 411 |
| 170 | 2-furylmethyl | $NCH_3$ | $CF_3$ | H | C | MH+ | 411 |
| 171 | (1-methyl-1H-pyrazol-4-yl)methyl | NH | $CF_3$ | H | C | MH+ | 411 |
| 172 | (1-methyl-1H-pyrazol-4-yl)methyl | O | $CF_3$ | H | C | MH+ | 412 |
| 173 | (1-methyl-1H-1,2,4-triazol-5-yl)methyl | NH | $CF_3$ | H | C | MH+ | 412 |
| 174 | 2-thiophenylmethyl | NH | $CF_3$ | H | C | MH+ | 413 |
| 175 | tetrahydro-2H-pyran-4-ylmethyl | NH | $CF_3$ | H | C | MH+ | 415 |
| 177 | (6-methyl-3-pyridyl)methyl | O | $C_2H_5$ | H | C | MH+ | 383 |
| 178 | 2,6-dimethyl-3-pyridyl | NH | $CF_3$ | H | C | MH+ | 422 |
| 179 | (6-methyl-3-pyridyl)methyl | NH | $CF_3$ | H | C | MH+ | 422 |
| 180 | 2-(6-methylpyridine)methyl | NH | $CF_3$ | H | C | MH+ | 422 |
| 181 | 6-ethyl-2-pyridyl | NH | $CF_3$ | H | C | MH+ | 422 |
| 183 | 2,6-dimethyl-3-pyridyl | O | $CF_3$ | H | C | MH+ | 423 |
| 184 | 2-(6-methylpyridine)methyl | O | $CF_3$ | H | C | MH+ | 423 |
| 185 | (2-methyl-3-pyridyl)methyl | O | $CF_3$ | H | C | MH+ | 423 |
| 186 | (6-methyl-3-pyridyl)methyl | O | $CF_3$ | H | C | MH+ | 423 |
| 187 | (1,3-dimethyl-1H-pyrazol-4-yl)methyl | NH | $CF_3$ | H | C | MH+ | 425 |

TABLE 1-continued

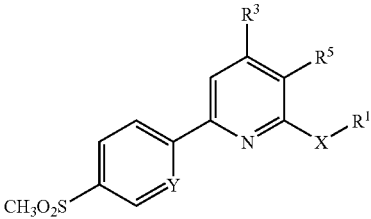

(I)

| Ex | R¹ | X | R³ | R⁵ | Y | MS | |
|---|---|---|---|---|---|---|---|
| 188 | (1,5-dimethyl-1H-pyrazol-4-yl)methyl | NH | CF₃ | H | C | MH+ | 425 |
| 189 | (4-methyl-1,3-thiazol-2-yl)methyl | NH | CF₃ | H | C | MH+ | 428 |
| 190 | (5-chloro-3-pyridyl) | O | CF₃ | H | C | MH+ | 429 |
| 191 | 6-chloro-3-pyridazinyl | NH | CF₃ | H | C | MH+ | 429/431 |
| 192 | (6-methyl-3-pyridyl)methyl | NH | CH₃ | CN | C | MH+ | 393 |
| 193 | benzyl | NC2H5 | CF₃ | H | C | MH+ | 435 |
| 196 | 2-carboxyphenyl | NH | CF₃ | H | C | MH+ | 437 |
| 197 | benzyl | NH | C₂H₅ | CO₂C₂H₅ | C | MH+ | 439 |
| 200 | (5-bromo-2-pyridyl)methyl | O | CF₃ | H | C | MH+ | 486/488 |
| 201 | (3-bromo-4-pyridyl)methyl | O | CF₃ | H | C | MH+ | 486/488 |
| 202 | (3-methyl-4-isoxazolyl)methyl | NH | CH₃ | H | C | MH+ | 358 |
| 203 | 5-pyrimidinylmethyl | NH | CH₃ | H | C | MH+ | 355 |
| 204 | (1-ethyl-1H-imidazol-2-yl)methyl | NH | C₂H₅ | H | C | MH+ | 385 |
| 205 | (1-methyl-1H-imidazol-2-yl)methyl | NCH₃ | CH₃ | CN | C | MH+ | 396 |
| 206 | cis-4-methylcyclohexyl | NH | CF₃ | H | C | MH+ | 413 |
| 207 | trans-4-methylcyclohexyl | NH | CF₃ | H | C | MH+ | 413 |
| 209 | cycloheptyl | NH | CF₃ | H | C | MH+ | 413 |
| 210 | 2-pyridylmethyl | NH | CH₃ | CN | C | MH+ | 379 |
| 211 | 1-ethylpropyl | NH | CF₃ | H | C | MH+ | 387 |
| 212 | cyclobutyl | NH | CF₃ | H | C | MH+ | 371 |
| 213 | (3-methyl-1,2,4-oxadiazol-5-yl)methyl | NH | CF₃ | H | C | MH+ | 413 |
| 214 | (5-methyl-1,2,4-oxadiazol-3-yl)methyl | NH | CF₃ | H | C | MH+ | 413 |
| 217 | 2-pyridylmethyl | O | C₂H₅ | CN | C | MH+ | 394 |
| 218 | (1-methyl-1H-pyrazol-5-yl)methyl | NH | CH₃ | H | C | MH+ | 357 |
| 221 | trans-4-(ethoxy)cyclohexyl | NH | CF₃ | H | C | MH+ | 443 |
| 223 | (5-methyl-2-pyridyl)methyl | NH | C₂H₅ | CN | C | MH+ | 407 |
| 224 | (6-methyl-3-pyridyl)methyl | NH | C₂H₅ | CN | C | MH+ | 407 |
| 225 | (1-methyl-1H-imidazol-2-yl)methyl | NH | C₂H₅ | CN | C | MH+ | 396 |
| 226 | (1-ethyl-1H-imidazol-2-yl)methyl | NH | C₂H₅ | CN | C | MH+ | 410 |
| 227 | (1-methyl-1H-imidazol-2-yl)methyl | NCH₃ | C₂H₅ | CN | C | MH+ | 410 |
| 228 | (1-methyl-1H-pyrazol-4-yl)methyl | NH | C₂H₅ | CN | C | MH+ | 396 |
| 229 | (4-methyl-1,3-thiazol-2-yl)methyl | NH | C₂H₅ | CN | C | MH+ | 413 |
| 230 | cyclohexyl | NH | C₂H₅ | CN | C | MH+ | 384 |
| 231 | cyclohexanemethyl | NH | C₂H₅ | CN | C | MH+ | 398 |
| 232 | (1-ethyl-1H-1,2,4-triazol-5-yl)methyl | NH | C₂H₅ | H | C | MH+ | 386 |
| 233 | (1-methyl-1H-1,2,4-triazol-5-yl)methyl | NH | C₂H₅ | H | C | MH+ | 372 |
| 235 | (1-ethyl-1H-1,2,4-triazol-5-yl)methyl | NH | CF₃ | H | C | MH+ | 426 |

TABLE 2

(I)

| Ex | R³ | R⁵ | Y | MS | |
|---|---|---|---|---|---|
| 65 | $C_2H_5$ | H | C | MH+ | 345 |
| 66 | $CH_3$ | $CH_3$ | C | MH+ | 345 |

TABLE 3

(I)

| Ex | R¹ | X | R³ | R⁵ | R¹⁰ | Y | MS | |
|---|---|---|---|---|---|---|---|---|
| 67 | benzyl | NH | $CH_3$ | H | F | C | MH+ | 371 |

TABLE 4

(I)

| Ex | R¹ | X | R³ | R⁵ | Y | MS | |
|---|---|---|---|---|---|---|---|
| 72 | n-butyl | NH | $CH_3$ | H | C | MH+ | 320 |
| 73 | 2-methylpropyl | NH | $CH_3$ | H | C | MH+ | 320 |
| 78 | cyclohexyl | NH | $CH_3$ | H | C | MH+ | 346 |
| 79 | benzyl | NH | $CH_3$ | H | C | MH+ | 354 |
| 90 | tetrahydro-2H-pyran-4-ylmethyl | NH | $CH_3$ | H | C | MH+ | 362 |
| 91 | tetrahydro-2H-pyran-4-yl | NH | $C_2H_5$ | H | C | MH+ | 362 |
| 102 | (6-methyl-3-pyridyl)methyl | NH | $CH_3$ | H | C | MH+ | 369 |
| 117 | (1,5-dimethyl-1H-pyrazol-4-yl)methyl | NH | $CH_3$ | H | C | MH+ | 372 |
| 118 | (1,3-dimethyl-1H-pyrazol-4-yl)methyl | NH | $CH_3$ | H | C | MH+ | 372 |
| 119 | (1-methyl-1H-pyrazol-4-yl)methyl | NH | $C_2H_5$ | H | C | MH+ | 372 |
| 127 | tetrahydro-2H-pyran-4-ylmethyl | NH | $C_2H_5$ | H | C | MH+ | 376 |
| 136 | (6-methyl-3-pyridyl)methyl | NH | $C_2H_5$ | H | C | MH+ | 383 |

TABLE 4-continued (I)

| Ex | R¹ | X | R³ | R⁵ | Y | MS | |
|---|---|---|---|---|---|---|---|
| 140 | (1,5-dimethyl-1H-pyrazol-4-yl)methyl | NH | $C_2H_5$ | H | C | MH+ | 386 |
| 141 | (1,3-dimethyl-1H-pyrazol-4-yl)methyl | NH | $C_2H_5$ | H | C | MH+ | 386 |
| 145 | (4-methyl-1,3-thiazol-2-yl)methyl | NH | $C_2H_5$ | H | C | MH+ | 389 |
| 146 | (5-chloro-2-pyridyl)methyl | NH | $CH_3$ | H | C | MH+ | 389/391 |
| 156 | 3-chloro-4-methylbenzyl | NH | $CH_3$ | H | C | MH+ | 402/404 |
| 157 | (5-chloro-2-pyridyl)methyl | NH | $C_2H_5$ | H | C | MH+ | 403/405 |
| 161 | benzyl | NH | $CF_3$ | H | C | MH+ | 408 |
| 176 | 3-chloro-4-methylbenzyl | NH | $C_2H_5$ | H | C | MH+ | 416/418 |
| 182 | 3,4-dichlorobenzyl | NH | $CH_3$ | H | C | MH+ | 422/424 |
| 194 | 3,4-dichlorobenzyl | NH | $C_2H_5$ | H | C | MH+ | 436/438 |
| 195 | 3,5-dichlorobenzyl | NH | $C_2H_5$ | H | C | MH+ | 436/438 |
| 199 | 4-chloro-3-(trifluoromethyl)benzyl | NH | $CH_3$ | H | C | [M − H] | 456 |

TABLE 5

(I)

| Ex | R⁵ | R⁸ | Y | MS | |
|---|---|---|---|---|---|
| 130 | H | $CH_3$ | C | MH+ | 382 |

Biological Data

Microsomal Assay

Inhibitory activity against microsomal h-COX2 was assessed against a microsomal preparation from baculovirus infected SF9 cells. An aliquot of microsomal preparation was thawed slowly on ice and a 1/40,000 dilution prepared from it into the assay buffer (sterile water, degassed with argon containing 100 mM HEPES (pH 7.4), 10 mM EDTA (pH7.4), 1 mM phenol, 1 mM reduced glutathione, 20 mg/ml gelatin and 0.001 mM Hematin). Once diluted the enzyme solution was then sonicated for 5 seconds (Branson sonicator, setting 4, 1 cm tip) to ensure a homogeneous suspension. 155 μl enzyme solution was then added to each well of a 96-well microtitre plate containing either 5 μl test compound (40× required test concentration) or 5 μl DMSO for controls. Plates were then mixed and incubated at room temperature for 1 hour. Following the incubation period, 40 µl of 0.5 µM arachidonic acid was added to each well to give a final concentration of 0.1 µM. Plates were then mixed and incubated for exactly 10 minutes (room temperature) prior to addition of 25 µl 1M HCl (hydrochloric acid) to each well to stop the reaction. 25 µl of 1M NaOH (sodium hydroxide) was then added to each well to neutralise the solution prior to determination of $PGE_2$ levels by enzyme immunoassay (EIA).

The following examples had $IC_{50}$ values for inhibition of COX-2 of 0.5 µM or less and at least a 100-fold selectivity for COX-2 over COX-1, based on comparison of the respective $IC_{50}$ values.

1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 43, 44, 45, 46, 47, 48, 49, 50, 51, 52, 53, 54, 55, 56, 57, 58, 59, 60, 61, 62, 63, 66, 67, 68, 69, 70, 72, 73, 74, 75, 76, 79, 80, 81, 82, 83, 84, 85, 86, 87, 88, 89, 90, 91, 92, 93, 94, 95, 96, 98, 99, 100, 101, 102, 103, 104, 105, 108, 109, 110, 112, 113, 114, 115, 116, 119, 120, 122, 123, 124, 125, 126, 127, 128, 129, 130, 131, 133, 134, 135, 137, 138, 139, 140, 141, 142, 143, 144, 145, 146, 147, 148, 149, 150, 151, 153, 154, 157, 158, 160, 161, 162, 163, 164, 165, 166, 167, 168, 169, 170, 171, 173, 174, 175, 177, 178, 180, 182, 183, 184, 185, 186, 187, 188, 189, 190, 191, 192, 193, 197, 200, 201, 202, 204, 205, 206, 207, 208, 209, 210, 211, 212, 213, 214, 215, 216, 217, 218, 219, 220, 221, 222, 223, 224, 228, 229, 231, 232, 233, 234, 235, 236.

The invention claimed is:

1. A compound of formula (I)

(I)

or a pharmaceutically acceptable salt thereof in which:

X is selected from the group consisting of oxygen and $NR^2$;

Y is CH;

$R^1$ is selected from the group consisting of H, $C_{1-6}$alkyl, $C_{1-2}$alkyl substituted by one to five fluorine atoms, $C_{1-3}$alkyl$OC_{1-3}$alkyl, $C_{3-6}$alkenyl, $C_{3-6}$alkynyl, $C_{3-10}$cycloalkyl$C_{0-6}$alkyl, $C_{4-7}$cycloalkyl substituted by $C_{1-3}$alkyl or $C_{1-3}$alkoxy, $C_{4-12}$bridged cycloalkyl, and $A(CR^6R^7)_n$;

$R^2$ is selected from the group consisting of H and $C_{1-6}$alkyl;

$R^3$ is selected from the group consisting of $C_{1-5}$alkyl and $C_{1-2}$alkyl substituted by one to five fluorine atoms;

$R^4$ is selected from the group consisting of $C_{1-6}$alkyl, $NH_2$ and $R^9CONH$;

$R^5$ is selected from the group consisting of hydrogen, $C_{1-3}$alkyl, $C_{1-2}$alkyl substituted by one to five fluorine atoms, $C_{1-3}$alkyl$O_2C$, halogen, cyano, $(C_{1-3}$alkyl$)_2NCO$, $C_{1-3}$alkylS and $C_{1-3}$alkyl$O_2S$;

$R^6$ and $R^7$ are independently selected from H and $C_{1-6}$alkyl;

A is an unsubstituted 6-membered aryl, or a 6-membered aryl substituted by one or more $R^8$;

$R^8$ is selected from the group consisting of halogen, $C_{1-6}$alkyl, $C_{1-6}$alkyl substituted by one more fluorine atoms, $C_{1-6}$alkoxy, $C_{1-6}$alkoxy substituted by one or more F, $NH_2SO_2$ and $C_{1-6}$alkyl$SO_2$;

$R^9$ is selected from the group consisting of H, $C_{1-6}$alkyl, $C_{1-6}$alkoxy, $C_{1-6}$alkyl$OC_{1-6}$alkyl, phenyl, $HO_2CC_{1-6}$alkyl, $C_{1-6}$alkyl$OCOC_{1-6}$alkyl, $C_{1-6}$alkylOCO, $H_2NC_{1-6}$alkyl, $C_{1-6}$alkyl$OCONHC_{1-6}$alkyl and $C_{1-6}$alkyl$CONHC_{1-6}$alkyl, $R^{10}$ is selected from the group consisting of H and halogen; and n is 0 to 4.

2. The compound of claim 1 or a pharmaceutically acceptable salt thereof, wherein $R^1$ is selected from the group consisting of H, $C_{1-6}$alkyl, $C_{1-2}$alkyl substituted by one to five fluorine atoms, $C_{1-3}$alkyl$OC_{1-3}$alkyl, $C_{3-6}$alkenyl, $C_{3-6}$alkynyl, $C_{3-10}$cycloalkyl$C_{0-6}$alkyl, $C_{4-12}$bridged cycloalkyl, and $A(CR^6R^7)_n$; and, $R^5$ is selected from the group consisting of hydrogen, $C_{1-3}$alkyl, $C_{1-2}$alkyl substituted by one to five fluorine atoms, halogen, cyano, $(C_{1-3}$alkyl$)_2NCO$, $C_{1-3}$alkylS and $C_{1-3}$alkyl$O_2S$.

3. The compound of claim 1 or a pharmaceutically acceptable salt thereof wherein n is 1 to 4.

4. A compound as claimed in claim 1 wherein:

X is oxygen;

Y is CH;

$R^1$ is $A(CR^6R^7)_n$;

$R^3$ is selected from the group consisting of $C_{1-5}$alkyl and $C_{1-2}$alkyl substituted by one to five fluorine atoms;

$R^4$ is $C_{1-6}$alkyl;

$R^5$ is selected from the group consisting of hydrogen, $C_{1-3}$alkyl, $C_{1-2}$alkyl substituted by one to five fluorine atoms, $C_{1-3}$alkyl$O_2C$, halogen, and $C_{1-3}$alkylS;

A is an unsubstituted 6-membered aryl, or a 6-membered aryl substituted by one or more $R^8$;

$R^8$ is selected from the group consisting of halogen, $C_{1-6}$alkyl, $C_{1-6}$alkyl substituted by one more fluorine atoms, $C_{1-6}$alkoxy, and $C_{1-6}$alkoxy substituted by one or more F;

$R^{10}$ is selected from the group consisting of H and halogen; and n is 0.

5. A compound selected from the group consisting of:

N-(cyclohexylmethyl)-6-[4-(methylsulfonyl)phenyl]-4-(trifluoromethyl)-2-pyridinamine;

N-cyclohexyl-6-[4-(methylsulfonyl)phenyl]-4-(trifluoromethyl)-2-pyridinamine;

N-cycloheptyl-6-[4-(methylsulfonyl)phenyl]-4-(trifluoromethyl)-2-pyridinamine;

N-(cis-4-methylcyclohexyl)-6-[4-(methylsulfonyl)phenyl]-4-(trifluoromethyl)-2-pyridinamine;

N-(1-ethylpropyl)-6-[4-(methylsulfonyl)phenyl]-4-(trifluoromethyl)-2-pyridinamine; and N-(cyclopentylmethyl)-6-[4-(methylsulfonyl)phenyl]-4-(trifluoromethyl)-2-pyridinamine.

6. A pharmaceutical composition comprising a compound as claimed in claim 1 in admixture with one or more physiologically acceptable carriers or excipients.

7. A method of treating an animal subject suffering from rheumatoid arthritis mediated by COX-2, which method comprises administering to said subject an effective amount of a compound as claimed in claim 1.

8. A method of treating an animal subject suffering from osteoarthritis mediated by COX-2, which method comprises administering to said subject an effective amount of a compound as claimed in claim 1.

9. A pharmaceutical composition comprising a compound as claimed in claim 2 in admixture with one or more physiologically acceptable carriers or excipients.

10. N-cyclohexyl-4-(trifluoromethyl)-6-[4-methylsulfonyl)phenyl]pyridine-2-amine or a pharmaceutically acceptable salt thereof.

* * * * *